(12) United States Patent
Morse et al.

(10) Patent No.: US 11,458,249 B2
(45) Date of Patent: Oct. 4, 2022

(54) BODY FLUID MANAGEMENT SYSTEMS FOR PATIENT CARE

(71) Applicant: BrainSpace, Inc., Camden, DE (US)

(72) Inventors: Stephen A. Morse, Woodinville, WA (US); Caitlin D. C. Morse, Woodinville, WA (US)

(73) Assignee: BrainSpace, Inc., Camden, DE (US)

( * ) Notice: Subject to any disclaimer, the term of this patent is extended or adjusted under 35 U.S.C. 154(b) by 0 days.

(21) Appl. No.: 17/466,301

(22) Filed: Sep. 3, 2021

(65) Prior Publication Data

US 2022/0062601 A1 Mar. 3, 2022

Related U.S. Application Data

(60) Provisional application No. 63/074,223, filed on Sep. 3, 2020.

(51) Int. Cl.
| | |
|---|---|
| *A61M 5/168* | (2006.01) |
| *A61M 27/00* | (2006.01) |
| *A61M 5/142* | (2006.01) |
| *A61M 25/00* | (2006.01) |
| *A61M 1/00* | (2006.01) |
| A61M 5/172 | (2006.01) |

(52) U.S. Cl.
CPC ........... *A61M 5/168* (2013.01); *A61M 1/772* (2021.05); *A61M 5/142* (2013.01); *A61M 25/0017* (2013.01); *A61M 27/00* (2013.01); *A61M 27/006* (2013.01); *A61M 2005/1726* (2013.01); *A61M 2202/0464* (2013.01); *A61M 2205/3334* (2013.01); *A61M 2205/505* (2013.01); *A61M 2209/088* (2013.01); *A61M 2230/30* (2013.01); *A61M 2230/62* (2013.01); *A61M 2230/63* (2013.01)

(58) Field of Classification Search
CPC .............................. A61M 27/00; A61M 5/168
See application file for complete search history.

(56) References Cited

U.S. PATENT DOCUMENTS

| | | |
|---|---|---|
| 8,608,716 B2 | 12/2013 | Holper |
| 9,717,890 B2 | 8/2017 | Holper |
| 10,413,710 B2 | 9/2019 | Lutz |

(Continued)

OTHER PUBLICATIONS

Avezaat, "Cerebrospinal Fluid Pulse Pressure and Intracranial Volume-Pressure Relationships," Journal of Neurology, Neurosurgery, and Psychiatry, 1979, pp. 687-700, vol. 42 [NPL_Avezaat].

(Continued)

*Primary Examiner* — Jenna Zhang
(74) *Attorney, Agent, or Firm* — Seed Intellectual Property Law Group LLP

(57) ABSTRACT

Provided are body fluid management systems for patient care that include, in operable combination, a control system assembly comprising a fluid flow detection and control subassembly, a user data interface, a patient interface assembly comprising a wearable pressure sensor subassembly having a pressure sensor in the path of said body fluid for attaching directly to a patient proximate to an anatomical marker and an orientation sensor to monitor and/or control the pressure and/or flowrate of a body fluid such as cerebrospinal fluid, blood, or urine.

18 Claims, 12 Drawing Sheets

(56) References Cited

U.S. PATENT DOCUMENTS

| | | | | |
|---|---|---|---|---|
| 2012/0078137 | A1* | 3/2012 | Mendels | G01F 23/2924 600/584 |
| 2012/0302938 | A1* | 11/2012 | Browd | A61M 39/284 604/9 |
| 2013/0197422 | A1* | 8/2013 | Browd | A61B 5/031 604/9 |
| 2017/0136209 | A1* | 5/2017 | Burnett | A61M 1/84 |
| 2017/0143880 | A1* | 5/2017 | Luxon | A61M 27/00 |
| 2017/0209056 | A1* | 7/2017 | Browd | G01L 9/0001 |
| 2018/0028794 | A1 | 2/2018 | Browd | |
| 2019/0126018 | A1 | 5/2019 | Browd | |
| 2019/0282742 | A1* | 9/2019 | El Katerji | A61B 5/7239 |

OTHER PUBLICATIONS

Beidler, "Fluidic Considerations of Measuring Intracranial Pressure Using an Open External Ventricular Drain," Cureus, 2021, p. e15325, vol. 13(5) [NPL_Beidler].

Bradley, "Cerebrospinal Fluid Pressure," J. Neurol. Neurosurg. Psychiat., 1970, pp. 387-397, vol. 33 [NPL_Bradley].

Bruce, "State-of-the-Art Review: Non-invasive Assessment of Cerebrospinal Fluid Pressure," Journal of Neuroophthalmology, 2014, pp. 288-294, vol. 34(3) [NPL_Bruce].

Czosnyka, "Monitoring and Interpretation of Intracranial Pressure," Journal of Neurology Neurosurgery, and Psychiatry, 2004, pp. 813-821, vol. 75 [NPL_Czosnyka].

Frazee, "Fluid Management for Critically Ill Patients: A Review of the Current State of Fluid Therapy in the Intensive Dare Unit," Kidney Disease, 2016, pp. 64-71, vol. 2 [NPL_Frazee].

Heldt, "Intracranial Pressure and Intracranial Elastance Monitoring in Neurocritical Care," Annual Review of Biomedical Engineering, 2019, pp. 523-549, vol. 21 [NPL_Heldt].

Kasprowicz, "Principles of Cerebrospinal Fluid Pressure-volume Compensation Revisited," Acta Neurologica Scandinavica, 2016, pp. 134(3), vol. 168 [NPL_Kasprowicz].

Kim, "Accuracy and Precision of Continuous Noninvasive Arterial Pressure Monitoring Compared with Invasive Arterial Pressure," Anesthesiology, 2014, pp. 1080-1097, vol. 120 [NPL_Kim].

Lee, "Cerebrospinal Fluid Pressure in Adults," Journal of Neuroophthalmology, 2014, pp. 278-283, vol. 34 [NPL_Lee].

Lutz, "New and Improved Ways to Treat Hydrocephalus: Pursuit of a Smart Shunt," Surgical Neurology International, 2013, pp. S38-S50, vol. 4 [NPL_Lutz].

Lyons, "Cebrospinal Fluid Physiology and the Management of Increased Intracranial Pressure," Mayo Clinic Proceedings, 1990, pp. 684-707, vol. 65 [NPL_Lyons].

Menacho, "Current Practices and Goals for Mean Arterial Pressure and Spinal Cord Perfusion Pressure in Acute Traumatic Spinal Cord Injury: Defining the Gaps in Knowledge," The Journal of Spinal Cord Medicine, 2021, pp. 350-356, vol. 44(3) [NPL_Menacho].

Padayachy, "Intracranial Pressure Monitoring for Traumatic Brain Injury in the Modem Era," Childs Nervous System, 2010, pp. 441-452, vol. 26 [NPL_Padayachy].

Raboel, "Intracranial Pressure Monitoring: Invasive Versus Non-invasive Methods—A Review," Critical Care Research and Practice, 2012, pp. 1-14, vol. 2012 [NPL_Raboel].

Raksin, "Noninvasive Intracranial Compliance and Pressure Based on Dynamic Magnetic Resonance Imaging of Blood Flow and Cerebrospinal Fluid Flow: Review of Principles, Implementation, and Other Noninvasive Approaches," Neurosurgeryl Focus, 2003, pp. 1-8, vol. 14 [NPL_Raksin].

Soler, "A Review of Cerebral Shunts, Current Technologies, and Future Endeavors," Yale Journal of Biology and Medicine, 2018, pp. 313-321, vol. 91 [NPL_Soler].

Steiner, "Monitoring the Injured Brain: ICP and CBF," Journal of Anaesthesiology, 2006, pp. 26-38, vol. 97 [NPL_Steiner_1].

Steiner, "Validation of a Tonometric Noninvasive Arterial Blood Pressure Monitor in the Intensive Care Setting," Anaesthesia, 2003, pp. 448-454, vol. 58 [NPL_Steiner_2].

Vagholkar, "Principles of Surgical Drainage," Surgery, 2000, pp. 45-47, vol. 4(12) [NPL_Vagholkar].

Van Der Jagt, "Fluid Management of the Neurological Patient: A Concise Review," Critical Care, 2016, pp. 126-136, vol. 20 [NPL_vanderJagt].

* cited by examiner

FIG. 3
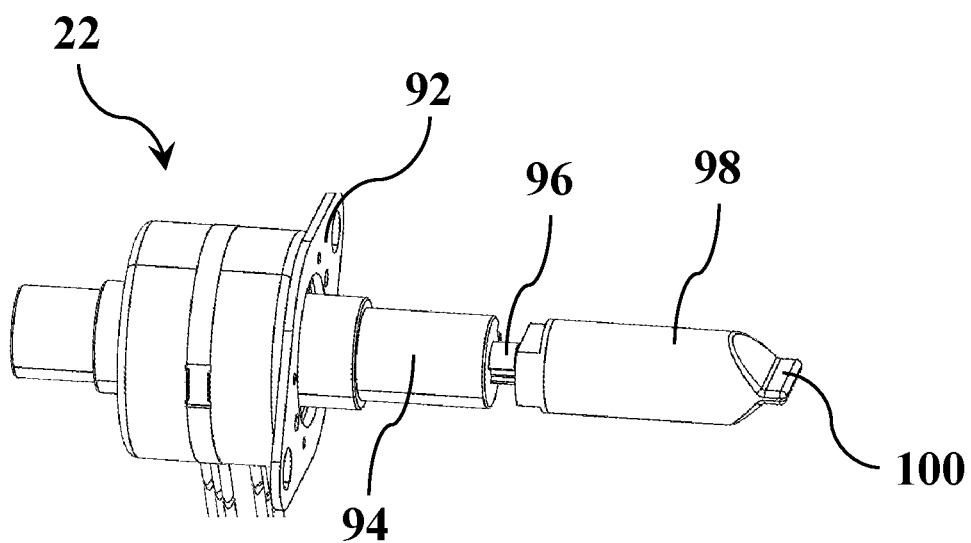
FIG. 3A
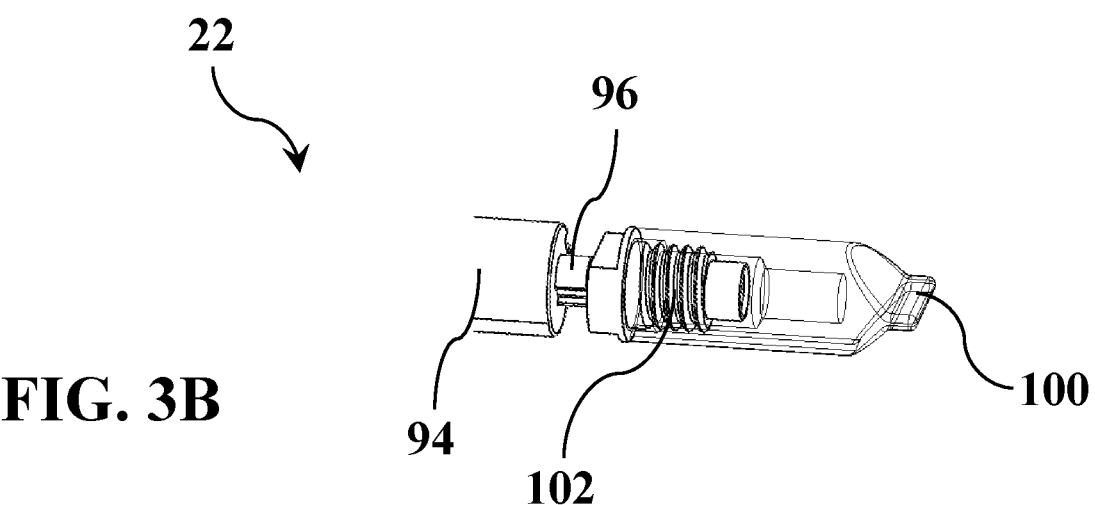
FIG. 3B

FIG. 9
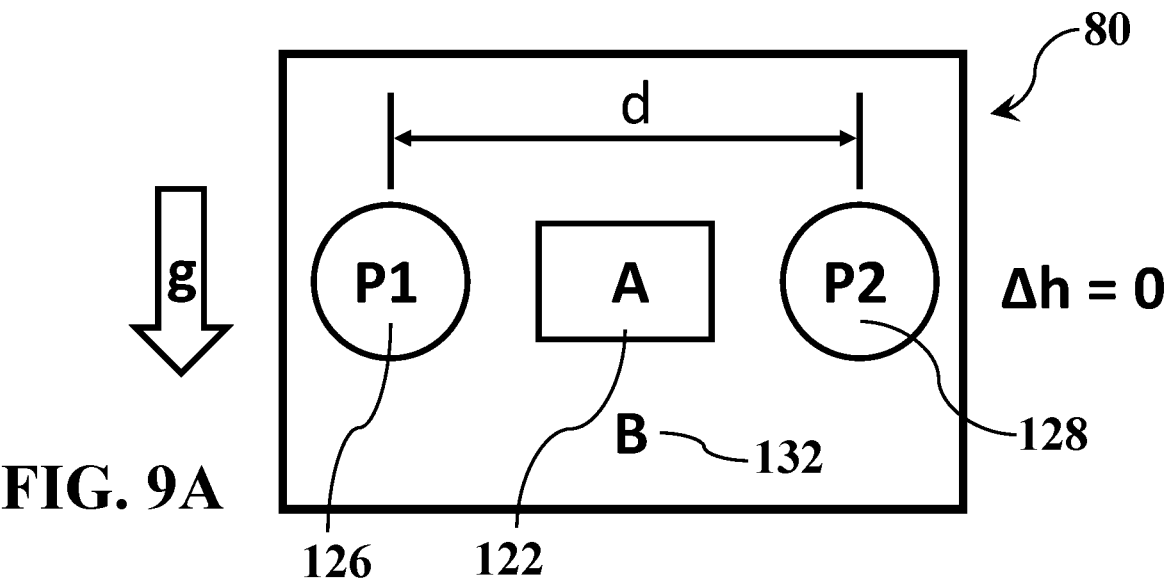
FIG. 9A
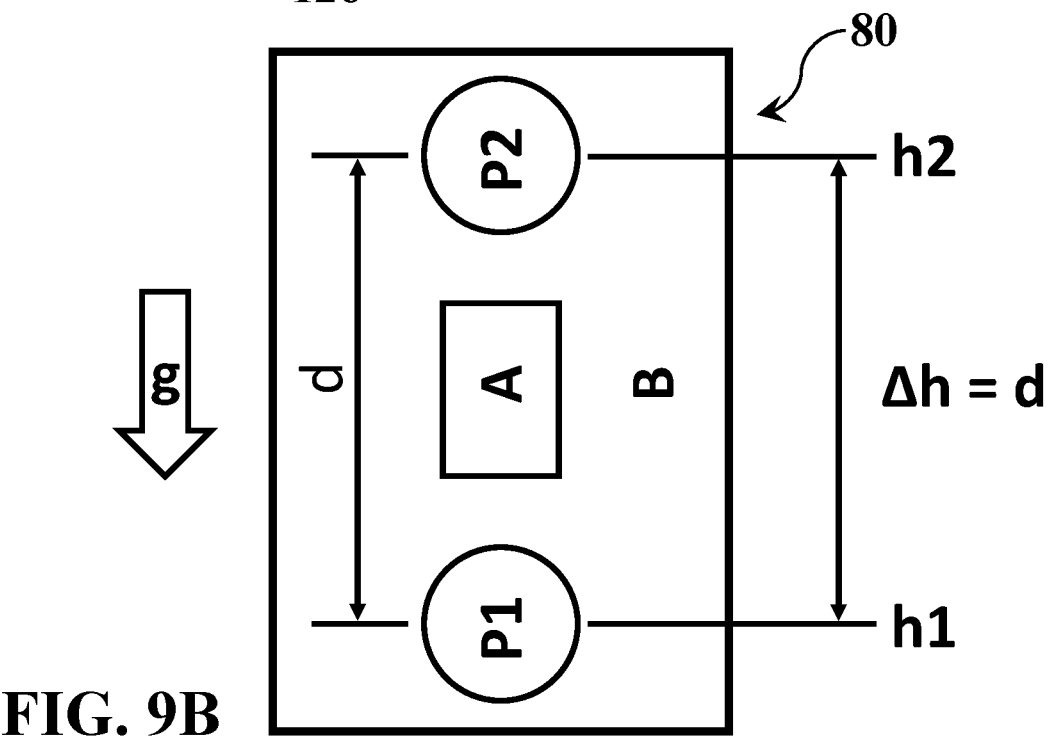
FIG. 9B

BODY FLUID MANAGEMENT SYSTEMS FOR PATIENT CARE

CROSS-REFERENCE TO RELATED APPLICATIONS

This U.S. non-provisional patent application was filed on Sep. 3, 2021 as U.S. patent application Ser. No. 17/466,301 and claims the benefit of U.S. Provisional Patent Application No. 63/074,223, which was filed on Sep. 3, 2020. The contents of U.S. Provisional Patent Application No. 63/074, 223 are incorporated herein by reference in their entirety.

BACKGROUND OF THE DISCLOSURE

Technical Field

The present disclosure relates, generally, to the field of medicine, in particular to medical devices, and associated procedures, for monitoring and/or controlling body fluid pressure, drainage flowrate, and patient movement. Disclosed herein are body fluid management systems for human and animal use, which provide real-time and integrated control of body fluid pressure and body fluid drainage flowrate that accommodate for frequent changes in the orientation and/or movement of a non-stationary patient.

Description of the Related Art

The medical benefits of managing body fluid pressures through the monitoring and controlled drainage of body fluids in a variety of clinical scenarios have been documented in the medical literature. This is particularly relevant where abnormal displacement, change in vessel wall compliance, excess production, or impaired natural drainage channels may cause an accumulation of body fluid within a single organ or body compartment. Excess body fluid within a single body compartment can cause elevated pressures, especially in low compliance conditions. Compartment syndrome is an elevation of intercompartmental pressure to a level that impairs circulation resulting in insufficient oxygenated blood supply leading to irreversible tissue ischemia and necrosis. See, e.g., Garner, *HSS J* 10(2):143 (2014); Keddissi, *Can. J. Respir. Ther.* 55 (2018); Marik, *Chest* 134:172-178 (2008); Trinooson, *AANA J* 81(5):357-368 (2013); Frazee, *Kidney Dis.* 2:64-71 (2016); Bhave, *J Am Soc Nephrol* 22:2166-2181 (2011); Bruce, *J Neuroophthalmol.* 34(3):288-294 (2014); van der Jagt, *Critical Care* 20:126 (2016); and Lee, *Neuro-Ophthalmol.* 34:278-283 (2014).

Risk factors associated with distinct causes of acute compartment syndrome by anatomical compartment have been identified in the medical literature. In the extremities, a fracture has been found to be the most common cause, with muscles and nerves being most at risk. In the brain, a number of causes have been identified, such as traumatic brain injury, stroke, infection, tumors, and congenital hydrocephalus. This is explained by the Monro-Kellie Doctrine, which establishes blood, cerebrospinal fluid and brain tissue, including interstitial fluid, as the primary variables driving pressure in the head. In the case of the peritoneal cavity, the most documented risk factor is a patient being critically ill. As many as 50% of critical care patients have been found to have elevated intra-abdominal pressure (IAP) putting them at risk for reduced abdominal organ perfusion and possible organ failure. Intra-abdominal hypertension (IAH) has also been found in clinical practice to impact lung function. As a result, monitoring of patients at risk for compartment syndrome has been adopted in addition to monitoring functions associated with treatment. See, Garner, *HSS J* 10(2): 143 (2014); Hunt, *J. Trauma Manag. Outcomes* 8:2 (2014); and Mokri, *Neurology* 56(12):1746 (2001).

Gravity-based drainage of bodily fluid, including as a treatment for elevated bodily pressure has been practiced for centuries, with significant improvements in the prior art over time. Unrestricted drains, such as urinary catheters, are intended to fully drain fluid from a body compartment and have been in use for 3500 years. Controlled partial drainage of cerebrospinal fluid to relieve pressure on the brain was first documented in 1744 by Claude-Nicholas Le Cat and methods were captured in the art by William Williams Keen in 1890. See, Feneley, *J ME&T* 39(8):459 (2015) and Srinivasan, *J Neurosurgery* 120:228 (2014).

The art was further advanced in 1927 with the addition of fluid pressure measurement to bodily fluid drainage with the introduction of the manometer. Manometers utilize the differential height of a column of fluid to measure pressure. When used in a medical context, a pole-mounted manometer is aligned to the height of an external anatomical marker with demonstrated clinical approximation to the compartment pressure being measured. In the case of intercranial pressure, the external auditory meatus or tragus of the ear is used when patient is in the supine position to approximate the Foramen of Monro in the brain. When measuring arterial pressure, the midaxillary line of the fourth intercostal space is typically used to approximate the heart. The device is then opened to atmospheric pressure to "zero" the system, which is to set the baseline level of the manometer from which the differential in the system will be determined. See, Srinivasan, *J Neurosurgery* 120:228 (2014) and Muralidharan, *Surg Neural Int* 6(Supp 6):S271 (2015).

Further advancements in the art allowed for manometers to be used as a single variable Boolean to control drainage of cerebrospinal fluid (CSF) based on the patient pressure being above or below a single target value. In this case, the outlet end is raised to the height of the target intracranial pressure (ICP) with the inlet end attached to a lumbar or ventricular catheter. When the pressure in the target compartment such as the skull or spinal column exceeds the back pressure created by the height of the water column in the outlet end, cerebrospinal fluid flows until balance is restored. In this way, this analog system is able to drain body fluid until the system reaches target pressure. See, Srinivasan, *J Neurosurgery* 120:228 (2014) and Muralidharan, *Surg Neurol Int* 6(Supp 6):S271 (2015).

While the use of manometers to control CSF drainage in this binary fashion is still common practice, external pressure transducer assemblies are now often connected to the outlet end of the manometer fluid line via a stopcock. When connected to pressure monitoring equipment, such as that used for invasive arterial blood pressure monitoring, this combination of products allows for intermittent measurement of the ICP value and visualization of the ICP waveform. This is accomplished by a clinical user manually pausing drainage and mechanically redirecting fluid to the pressure monitoring system using the stopcock.

Despite advances in the art over the last hundred years, limitations and risks present in existing systems represent an unmet need in the art of bodily fluid management systems. Because manometers are dependent on alignment of pole-mounted fluid column height to the anatomical reference, these systems are dependent on stationary patients. Given the low-pressure column heights relative to the height of the patient anatomy, manometers are very sensitive to patient position and movement. Even minor changes in patient position such as turning the head, adjusting the patient to reduce pressure injuries, or changes in head of bed positioning can result in rapid over/under drainage leading to disability or death. As a result, these systems must be constantly maintained and adjusted to compensate for any patient movement. Often it is logistically simpler to keep the patient sedated, which presents numerous medical risks and other drawbacks for the patient, family, and healthcare provider. Even so, the risk inherit in manometer-based drainage necessitates constant clinical supervision. Medical publications have pointed to the improved outcomes possible with early mobility post-stroke and how to work around existing technology limitations to do so. This indicates that an invention more conducive to patient movement could contribute to lower rates of long-term disability. See, e.g., Azuh, *Am J Med* 129(8):866 (2016) and Mulkey, *J Neuroscience* 46(3):153 (2014).

More broadly, manometers lack the ability for a user to select a desired flowrate and current practice involves manually adjusting the target pressure up and down until a desired flowrate is approximated achieved indirectly. Manometers do not monitor drainage volume or provide any closed-loop behavior. They require visual estimation and manual annotation of drained volume by the clinical user rather than automated, quantitative monitoring and reporting. In clinical use, this is known to result in varying levels of precision dependent on user technique. Furthermore, manometer drainage systems suffer from highly variable resistance to flow, which causes inconsistent and unreliable drainage—a phenomenon that is well documented in public training materials for such devices. In these systems, drainage should initiate anytime the inlet pressure to the manometer exceeds the back pressure created by the height of the water column in the manometer.

For example, if a patient has been maintained at equilibrium at 10cmH2O, then ICP suddenly spikes to 15cmH2O, the manometer should overflow and begin to drain to restore pressure equilibrium to the 10cmH2O set point. However, in order to initiate (or maintain) flow in the drainage line, the fluid must overcome the resistance to flow along the entire length of the drain line. Since resistance to flow can be strongly influenced by bits of tissue, air gaps, or large bubbles in the drain line, micro bubbles adhered to the inner wall of the drain line, manufacturing variation in components and assembly operations (tolerances, adhesive pushout during bonding operations, etc.), and a variety of other factors, drainage may not initiate until after ICP has increased considerably beyond the desired set point, and may cease well before the set point equilibrium is restored. Because ICP values are so small in absolute terms, the resistance to flow can be quite large relative to clinically significant ICP changes. The observed unreliable and inconsistent drainage is largely unavoidable due to the physics of manometer-based drains.

Manometers and external pressure transducers can be paired (as is often done clinically) to construct a fluid management system that provides fluid pressure monitoring as well as fluid drainage; however, such fluid management systems cannot be used to simultaneously measure fluid pressure while controlling fluid drainage. As a result, this pairing lacks the ability to offer continuous monitoring and drainage, increasing the risk of complications not being detected in a timely manner.

The existing art does include the recent addition of new more complex catheters that allow for pressure transducer assemblies to be connected to the catheter in parallel with the drainage manometer to allow for continuous monitoring. This approach creates non-communicating, parallel activities displayed to the user, rather than an integrated system. This approach still depends on a manometer to control drainage based on a Boolean threshold, including the manometer limitations therein.

Existing external pressure monitoring technologies suffer from drift resulting in a lack of accuracy that is particularly relevant in the anatomical compartments for which the pressure is represented by small numerical values and even minor changes within a narrow range are of clinical significance. In most mammals, this would include a variety of compartment pressures such as ICP, CVP, IAP and the like. These values are measured in millimeters of mercury (mmHg) or centimeters of water (cmH2O). When considering ICP in humans for example, infant normal is often expressed as <5 mmHg while supine adults are typically 7-15 mmHg depending on the patient. In the case of IAP, normal adult values are 5-7 mmHg and in children are typically 0-5 mmHg. This is in comparison with arterial pressure values in a much wider range of 60-120 mmHg. In clinical practice, they have a typical accuracy on the order of ±2 mmHg in practical use due to sensor drift. However, clinically significant deviations in various pressure parameters of interest (ICP, CVP, IAP, etc.) are on the order of a few cmH2O. Therefore, the results derived from these sensors are at best of delayed clinical use until the patient worsens further, and at worst misleading. Given the importance of the brain, heart and other organ function to not only recovery from acute illness, but long-term quality of life of the patient, early detection of true changes in values would be a significant improvement over the prior art.

Diaphragm-style transducers more recently introduced to obtain clinically relevant accuracy generally have lower natural resonant frequencies and may suffer from undesired oscillations induced by physiological functions such as a heartbeat.

Due to inability of all these systems to detect sensor drift or failure, such systems necessarily rely on complicated schemes, custom sensor configurations, or constant manual recalibration to temporarily achieve the precision and accuracy required to provide existing clinical benefit. These labor-intensive accommodations along with the risks they introduce have throttled more widespread adoption of the core bodily fluid drainage technology.

Another shortcoming of the existing inventions is in the area of perfusion pressure (i.e., the net pressure of fluid passing through the circulatory system or lymphatic system into an organ or tissue (generally, an anatomical compartment). Perfusion pressure includes cerebral perfusion pressure (CPP), which is the net pressure gradient causing cerebral blood flow to the brain (brain perfusion). It must be maintained within narrow limits because too little pressure could cause brain tissue to become ischemic (having inadequate blood flow), and too much could raise intracranial pressure (ICP).

Measurements of perfusion pressure are clinically relevant to managing compartment pressure and preventing a compartment syndrome in which increased pressure within one of the body's anatomical compartments results in insufficient blood supply to tissue within that space. See, Peitzman, *The Trauma Manual: Trauma and acute Care Surgery* (Lippincott Williams & Wilkins, 2012)). Individual fluid pressures are often inputs into the clinical management of perfusion pressure and are used in the mathematical formula for calculating perfusion pressure (i.e. Spinal Fluid Perfusion Pressure=MAP−lumbar pressure). There remains a need in the art for automation of activities and calculations, which are currently being performed by a clinician such as a nurse using multiple systems and human analysis.

When calculating perfusion pressure, the MAP value is typically obtained from the invasive arterial blood pressure monitor which nurses are trained to align with the midaxillary line and fourth intercostal space as these are the anatomical markers for the location of the heart. While the patient is in the supine position, the height of the fluid column driving pressure is going to be fairly constant across the horizontal plane. However, patients are often adjusted to 30-degree Head of Bed position. In this position, MAP values are going to be calculated differently if referencing the anatomical marker of the compartment fluid versus that of the heart. The inconsistencies in the practice and even among nurse educators create variability in the calculated CPP values due to patient position. This can lead to adverse outcomes and thwart medical innovation.

Furthermore, perfusion pressure is calculated by a patient monitor as the result of multiple devices providing values in parallel unidirectionally to the display. This monitoring and communication function is occurring completely separate from drainage. The existing art does not support integrated multi-modal analysis and management. It has no ability to control drainage based on these calculated perfusion pressure values.

When considering perfusion pressure in clinical context, the inability in the prior art to sense or characterize patient movement results in unexpected opportunities for improvement beyond real-time drainage accuracy. For example, current systems cannot distinguish between clinically indicative changes in compartment pressure versus expected, predictable changes due to change in patient position or movement. This currently requires immediate nursing response to alarms if in use, creating alarm fatigue. It also requires manual annotation in the patient data in order for trend information to be useful in assessing patient's condition. It does not offer an efficient method for mapping impact of patient movement or position on compartment pressures. Finally, it obscures otherwise useful datasets that could advance the art in terms of bodily fluid management or broader medical understanding.

When the primary purpose of bodily fluid drainage is not to achieve a specific pressure value, other analog devices are available for use in draining body fluids. Excluding the use of syringes used in manual fluid sampling, the existing systems are also gravity-based and can be described as volume-limiting drains and unrestricted drains. Volume-limiting drains are fully disposable analog catheters that depend on the mechanical constraint of a full bulb to stop drainage. In comparison with manometers, which are typically connected to a drain bag that can hold more than 500 ml of fluid, volume-limiting catheters may only have a capacity for 30 ml and are removed upon completion of draining 30 ml. Unrestricted drains, such as urinary catheters, surgical drains, or wound management devices, are also analog catheters which are intended to fully drain fluid from a body compartment. They may be indwelling or used intermittently. Neither volume-limiting drains nor unrestricted drains can be used to measure pressure, and neither can drain fluids based upon a target pressure. Both also lack the ability for a user to designate a desired flowrate despite speed of drainage being a significant variable clinicians would prefer to control by patient condition. These various analog drain systems also require visual estimation of volume drained using markings on the drain bag as they lack quantitative calculation and reporting of volume drained.

While existing body fluid management systems provide some clinical benefit, particularly when multiple devices are used in combination, the need remains for integrated systems for real-time fluid pressure monitoring and control of fluid drainage that allow for patient movement without requiring constant medical oversight or intervention. Thus, there remains an unmet need in the art for body fluid management systems that permit the monitoring and management of body fluid pressures in non-stationary patients.

SUMMARY OF THE DISCLOSURE

The present disclosure fulfills unmet needs in the art, and further related advantages over existing technologies, by providing body fluid management systems that employ digital technologies to permit real-time monitoring and control of body fluid pressures or drainage flowrates while allowing or accounting for patient movement. Use of the various sensing modalities in combination enables improved accuracy, control, data capture, patient safety, and patient mobility relative to the systems described in the prior art. Furthermore, the integration of drainage control and multi-fluid pressure monitoring into a single system enables automated therapeutic intervention based on derived physiological parameters, such as perfusion pressure, which is unprecedented in the art.

Thus, within certain embodiments, the present disclosure provides body fluid management systems, comprising: a control system assembly for real-time monitoring of body fluid pressure and integrated control of body fluid drainage and a patient interface assembly comprising a wearable pressure sensor subassembly for attaching proximate to a patient anatomical marker, said wearable pressure sensor subassembly comprising a pressure sensor in the path of said body fluid and an orientation sensor. In some aspects, control system assemblies are configured for detecting changes in body fluid pressure, patient movement, or patient orientation based on inputs from the patient interface assembly. In other aspects, control system assemblies are configured with an algorithm to make corrective adjustments to the flowrate of body fluid drainage or assert an alarm based on user-defined settings.

In certain aspects of these embodiments, body fluid management systems comprise a control system assembly having a fluid flow detection and control subassembly in operable communication with a user interface subassembly including graphical user interface, such as a graphical user interface configured to display a pressure waveform. In related aspects, the fluid flow detection and control subassembly comprises, in operable communication, a flowrate control actuator, a flow shutoff actuator, and a body fluid flow detector.

In other aspects of these embodiments, body fluid management systems comprise a wearable pressure sensor subassembly having a plurality of pressure sensors in the body fluid path, wherein the plurality of pressure sensors comprises a first pressure sensor and a second pressure sensor at a fixed spacing distance and wherein the plurality of pressure sensors and said orientation sensor are configured on a rigid member for detecting drift in one or more of said plurality of pressure sensors based on a disparity between an anticipated differential pressure between the first pressure sensor and the second pressure sensor and an actual differential pressure between the first pressure sensor and the second pressure sensor.

In related aspects of these embodiments, body fluid management systems comprise a patient interface assembly having a body fluid drip chamber, a fluid drainage cartridge for connecting to said control system assembly, a drain tube for body fluid drainage, and an electrical cable for passing signals from said wearable pressure sensor subassembly to said fluid drainage cartridge.

In certain of the body fluid management systems disclosed herein, the body fluid is cerebrospinal fluid (CSF) and the control system assembly is configured for real-time monitoring of intracranial pressure (ICP) and integrated control of CSF drainage. In related aspects, the patient interface assembly comprises a drain tube that is configured at its proximal end for connecting to a ventricular catheter and a wearable pressure sensor subassembly that is configured for attaching proximate to a patient external auditory meatus (EAM).

In related embodiments, the body fluid management systems disclosed herein further comprise an infusion source configured for connecting to the control system assembly via a bidirectional infusion and drainage tube, wherein the control system assembly comprises a pump for pumping liquid from the infusion source to a body cavity. In certain aspects of these embodiments, the control system assembly is configured for real-time monitoring of intra-abdominal pressure and the patient interface assembly comprises a drain tube that is configured at its proximal end for connecting to a urinary catheter. In other aspects, the body cavity is a bladder.

In further embodiments of the present disclosure are provided systems for determining perfusion pressure, that comprise a control system assembly for real-time monitoring of body fluid pressure and integrated control of body fluid drainage from a body compartment, wherein the control system assembly is configured with a pump for pumping a fluid from an infusion source into secondary fluid line described below, and an algorithm to respond to signals from a first wearable pressure sensor subassembly and a second wearable pressure sensor subassembly to make corrective adjustments to the flowrate of body fluid drainage or assert an alarm based on user-defined settings.

The systems for determining perfusion pressure according to these embodiments comprise a patient interface assembly having a primary fluid line that is configured at its proximal end for connecting to a catheter inserted into said body fluid compartment and at its distal end for connecting to a detachable fluid drainage reservoir, a first wearable pressure sensor subassembly for attaching proximate an anatomical marker for the body fluid compartment, wherein the first wearable pressure sensor subassembly comprises a first pressure sensor in the path of the body fluid and an orientation sensor that are configured for detecting changes in body fluid pressure and patient movement and orientation and signaling those changes to said control system assembly, a secondary fluid line that is configured at its proximal end for connecting to an arterial catheter and at its distal end for connecting to said infusion source, a second wearable pressure sensor subassembly for attaching proximate an anatomical marker for monitoring blood pressure, wherein said second wearable pressure sensor subassembly comprises a second pressure sensor in the path of said blood and an orientation sensor that are configured for detecting changes in blood pressure and patient movement and orientation and signaling those changes to said control system assembly, wherein perfusion pressure is calculated based on the measured blood pressure and body compartment fluid pressure.

Within certain aspects of these embodiments, control system assemblies comprise a fluid flow detection and control subassembly in operable communication with a user interface subassembly including graphical user interface, such as a graphical user interface that is configured to display a pressure waveform. In related aspects fluid flow detection and control subassemblies comprise, in operable communication, a flowrate control actuator, a flow shutoff actuator, and a body fluid flow detector.

Within other aspects of these embodiments, the first wearable pressure sensor subassembly comprises a first pressure sensor and a second pressure sensor in a body fluid path, wherein the first and second pressure sensors are at a fixed spacing distance, and wherein the first and second pressure sensors and the orientation sensor are configured on a rigid member for detecting drift in the first pressure sensor or the second pressure sensor based on a disparity between an anticipated differential pressure between the first and second pressure sensors and an actual differential pressure between the first and second pressure sensor.

Within further aspects of these embodiments, the second wearable pressure sensor subassembly comprises a third pressure sensor and a fourth pressure sensor in the blood path, wherein the third and fourth pressure sensors are at a fixed spacing distance, and wherein the third and fourth pressure sensors and the orientation sensor are configured on a rigid member for detecting drift in the third pressure sensor or the fourth pressure sensor based on a disparity between an anticipated differential pressure between the third and fourth pressure sensors and an actual differential pressure between the third and fourth pressure sensors.

Within related aspects, the patient interface assembly comprises a body fluid drip chamber, a fluid drainage cartridge for connecting to the control system assembly, a drain tube for body fluid drainage, and an electrical cable for passing signals from the wearable pressure sensor subassembly to the fluid drainage cartridge.

Within other aspects, the body fluid is cerebrospinal fluid (CSF), the control system assembly is configured for real-time monitoring of intracranial pressure (ICP) and integrated control of CSF drainage, the patient interface assembly comprises a drain tube that is configured at its proximal end for connecting to a ventricular catheter, and the wearable pressure sensor subassembly is configured for attaching proximate to a patient external auditory meatus (EAM).

Within further aspects, systems according to these embodiments comprise a connection for an infusion source and a bidirectional infusion and drainage tube, wherein the control system assembly comprises a pump for pumping liquid from the infusion source to a body cavity. In related aspects, the control system assembly is configured for real-time monitoring of intra-abdominal pressure and the patient interface assembly comprises a drain tube that is configured at its proximal end for connecting to a urinary catheter. In other aspects, the body cavity is a bladder.

The present disclosure also provides wearable pressure sensor subassemblies that comprise a plurality of pressure sensors in the path of a body fluid and an orientation sensor, wherein the plurality of pressure sensors and the orientation sensor are configured for detecting changes in body fluid pressure, patient movement, or patient orientation. In certain aspects, the wearable pressure sensor subassembly is configured for attaching proximate to a patient anatomical marker. In other aspects, the plurality of pressure sensors comprises a first pressure sensor and a second pressure sensor at a fixed spacing distance and the plurality of pressure sensors and the orientation sensor are configured on a rigid member for detecting drift in the first pressure sensor and the second pressure sensor based on a disparity between an anticipated differential pressure between the first pressure sensor and the second pressure sensor and an actual differential pressure between the first pressure sensor and the second pressure sensor.

Within further aspects of these embodiments, wearable pressure sensor subassemblies are configured for attaching to a patient external auditory meatus (EAM) and the plurality of pressure sensors and the orientation sensor are configured for detecting changes in intracranial pressure (ICP).

The various fluid management systems disclosed herein provide particular advantages for the monitoring and control of body fluid pressures and flowrates in mobile patients where real-time monitoring of body fluid pressures and integrated control of body fluid drainage flowrates yields improved patient care through enhanced automation, greater opportunity for patient mobility, and reduced reliance on health care professionals for continual fluid pressure monitoring and system calibration as is required of fluid pressure management systems that are currently available in the art.

These and other related aspects of the present disclosure will be better understood in view of the following drawings and detailed description, which exemplify certain aspects of the various embodiments.

BRIEF DESCRIPTION OF THE DRAWINGS

Certain aspects of the present disclosure will become more evident in reference to the drawings, which are presented for illustration, not limitation.

FIG. 3 (FIG. 3A and FIG. 3B) are line drawings showing perspective views of an exemplary flowrate control actuator for use in control system assemblies according to certain embodiments of the presently disclosed body fluid management systems. The flowrate control actuator shown in FIG. 3A employs a pinch head that is fixedly attached to a leadscrew. The flowrate control actuator shown in FIG. 3B employs a spring-loaded pinch head.

As shown in FIG. 4, patient interface assemblies are configured for removable insertion into, and operable combination with, a control system assembly, such as, for example, a control system assembly as depicted in FIG. 1 and FIG. 2.

FIG. 9 (FIG. 9A and FIG. 9B) is a schematic representation of a wearable pressure sensor subassembly according to certain embodiments of the present disclosure.

DETAILED DESCRIPTION OF THE DISCLOSURE

Figure 1:
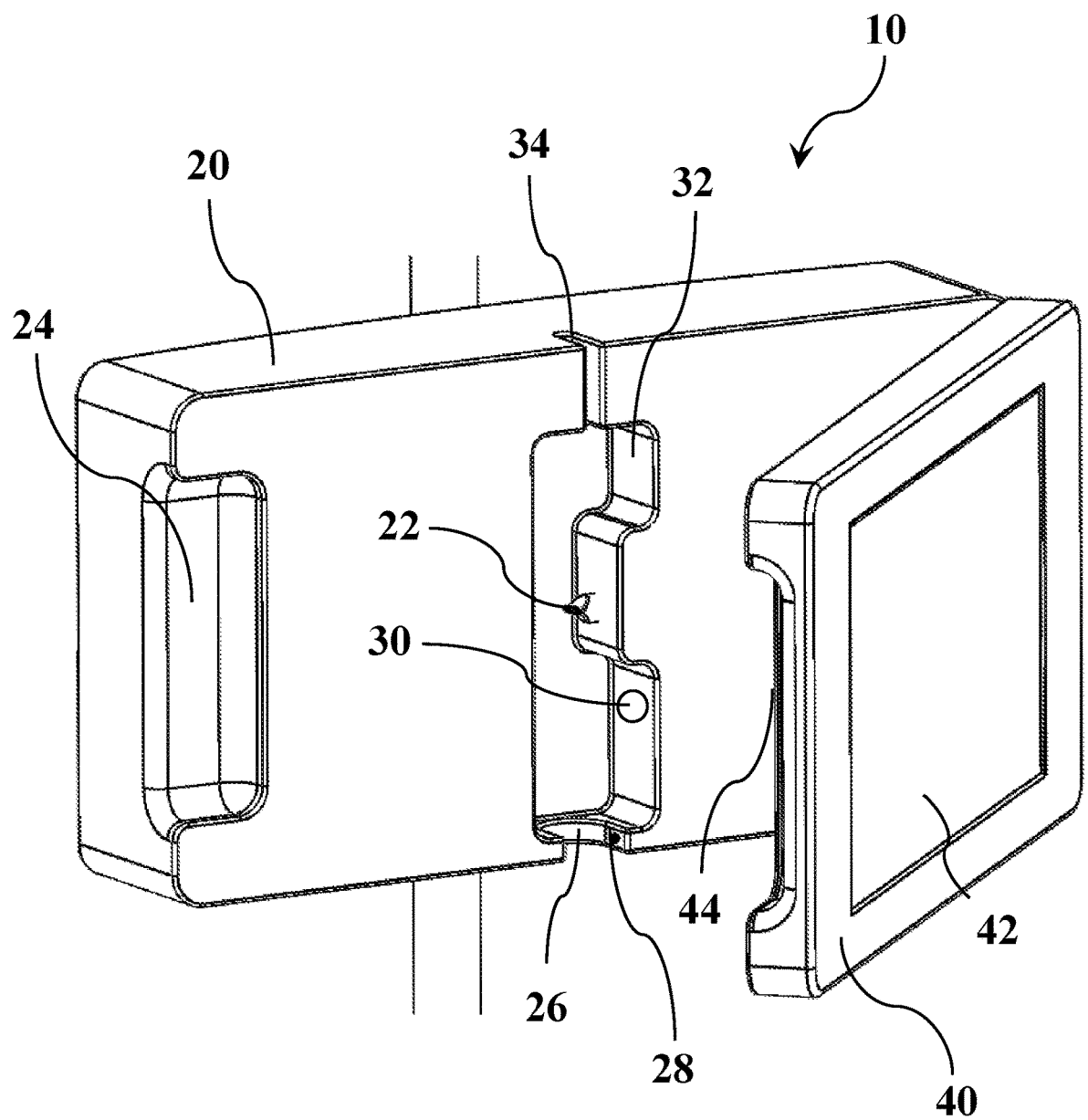
FIG. 1 is a line drawing showing a front perspective view of a control system assembly according to certain embodiments of the presently disclosed body fluid management systems. Control system assemblies according to these embodiments are configured for use in operable combination with a patient interface assembly (such as is depicted in FIG. 4 and described in further detain herein).

The present disclosure provides body fluid management systems that employ digital technologies to permit real-time monitoring and control of body fluid pressures or drainage flowrates while allowing or accounting for patient movement. Within certain embodiments, portable systems according to the present disclosure comprise, in operable combination, (1) a control system assembly and (2) a patient interface assembly. The body fluid management systems disclosed herein exhibit unexpected and surprising advantages over devices and technologies that are currently available in the art for monitoring and managing in vivo fluid pressures and flowrates.

This disclosure will be better understood in view of the following definitions, which are provided for clarification and are not intended to limit the scope of the subject matter that is disclosed herein.

Definitions

Unless specifically defined otherwise herein, each term used in this disclosure has the same meaning as it would to those having skill in the relevant art.

As used herein, the term "body fluid" refers generally to liquids within an extracellular compartment of the human body (i.e. extracellular fluids (ECF)), which include both interstitial fluids that are not contained within blood vessels and intravascular fluids that are contained within the blood vessels (such as venous fluids and arterial fluids). As used herein, "body fluids" include fluids within the transcellular compartment, such as fluids in the tracheobronchial tree, the gastrointestinal tract, and the bladder, and includes cerebrospinal fluid and fluids within the aqueous humor of the eye.

As used herein, the term "cerebrospinal fluid" or "CSF" refers to the sodium-rich, potassium-poor tissue fluid of the brain and spinal cord. CSF supplies nutrients, removes waste products, and provides a cushion that absorbs mechanical shock to the central nervous system. CSF is normally watery, clear, colorless, and almost entirely free of cells. A normal adult human has about 125-150 mL of CSF circulating within the ventricular system of the brain and spine. The majority of CSF is produced from within the two lateral ventricles.

As used herein, the term "body fluid pressure" refers generally to the pressure exerted by a "body fluid" that is contained within an extracellular compartment and includes, for example, intracranial pressure, arterial pressure, central venous pressure, and intra-abdominal pressure/bladder pressure.

As used herein, the term "body compartment pressure" refers generally to the pressure within an extracellular compartment and includes, for example, the pressure within the head (intracranial pressure), the abdomen (intra-abdominal pressure) and the limbs.

As used herein, the terms "compartment syndrome" and "compartment hypertension" refer to abnormally elevated pressure within a body compartment. "compartment hypertension" is characterized by a lower disease threshold as compared to "compartment syndrome."

As used herein, the term "intracranial pressure" or "ICP" refers to the pressure exerted by the cerebrospinal fluid (CSF) inside the skull and on the brain tissue.

As used herein, the term "arterial pressure" refers to the blood pressure in the arterial vasculature. The term is generally synonymous with the related term "mean arterial pressure" (MAP), which refers to the average blood pressure in an individual over a single cardiac cycle. MAP is calculated using the systolic pressure (SP) peak during heart pumping/squeeze and diastolic pressure (DP) low during heart relaxing between pumps/beats, according to the expression MAP=DP+(SP−DP)/3.

As used herein, the term "central venous pressure" or "CVP" refers to the blood pressure in the vena cava, near the right atrium of the heart.

As used herein, the term "accelerometer" refers to a type of "orientation sensor" that is capable of quantifying acceleration in one or more axial directions, according to the inertial force of a mass and Newton's Second law, and producing a digital electrical signal (SPI, I2C, etc.) proportional to said acceleration. Such devices are useful for determining orientation (by measuring static acceleration due to gravity) and detecting motion (by analyzing dynamic acceleration).

As used herein, the term "pressure sensor" refers to a device that is capable of quantifying pressure (and changes in pressure) in a fluid (air, water, saline, body fluid, etc.) and producing an electrical signal proportional to said pressure (or change in pressure). As used herein, "pressure sensor" may refer to a device configured to measure gauge pressure or absolute pressure.

As used herein, the term "anatomical marker" refers to physiological attributes or features that are non-invasively identifiable, such as cephalometric landmarks, joints, or intercoastal space and the like, for which there may be clinical significance relative to an internal position. Examples include: the external auditory meatus (EAM) or the glabella as anatomical markers for the brain center or Foramen of Monro often used in the calculation of ICP, and the fourth intercostal space at the midaxillary line as an anatomical marker for the position of the heart.

Words and phrases using the singular or plural number also include the plural and singular number, respectively. For example, terms such as "a" or "an" and phrases such as "at least one" and "one or more" include both the singular and the plural. Terms that are intended to be "open" (including, for example, the words "comprise," "comprising," "include," "including," "have," and "having," and the like) are to be construed in an inclusive sense as opposed to an exclusive or exhaustive sense. That is, the term "including" should be interpreted as "including but not limited to," the term "includes" should be interpreted as "includes but is not limited to," the term "having" should be interpreted as "having at least."

The use of the term "or" in the claims and supporting text is used to mean "and/or" unless explicitly indicated to refer to alternatives only or the alternatives are mutually exclusive, although the disclosure supports a definition that refers to only alternatives and "and/or."

Additionally, the terms "herein," "above," and "below," and words of similar import, when used in this application, shall refer to this application as a whole and not to any particular portion of the application.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

All references cited herein, whether supra or infra, including, but not limited to, patents, patent applications, and patent publications, whether U.S., PCT, or non-U.S. foreign, and all technical, medical, and/or scientific publications are hereby incorporated by reference in their entirety.

Body Fluid Management Systems

Provided herein are body fluid management systems that employ digital technologies to permit real-time integrated monitoring and control of body fluid pressures or drainage flowrates while allowing or accounting for patient movement.

Exemplary body fluid management systems disclosed herein are described in reference to the management of particular body fluid(s). It will be understood, however, that the body fluid management systems of the present disclosure will find utility in the monitoring and management of various extracellular and interstitial body fluids including, without limitation, cerebrospinal fluid, blood, urine, wound exudate, mucus, and semen. Furthermore, it will be understood that the body fluid management systems of the present disclosure will find utility in the monitoring and management of various bodily compartments including, without limitation, the intracranial space, the intra-abdominal space, and the extremities.

Within certain embodiments, body fluid management systems according to the present disclosure comprise, in operable combination, (1) a control system assembly and (2) a patient interface assembly.

In certain aspects of these embodiments, the control system assembly may be durable and the patient interface assembly may be disposable. In other aspects, the body fluid management systems disclosed herein may be fully durable with a cleanable or re-sterilizable patient interface assembly, or such systems may be fully disposable.

The body fluid management systems disclosed herein may be selectively operable in a pressure-control mode (e.g., by utilizing a pressure set point), in a flowrate-control mode (e.g., by utilizing a drainage flowrate set point), or in a monitoring-only mode for pressure data collection or user notifications (e.g., alarms) in response to user-configurable alarm thresholds.

Flowrate-control mode and pressure-control mode may both be accomplished in the same manner: by controlling the drainage of the associated body fluid. This may be accomplished by means of a soft flexible tube in the patient interface assembly that is variably or intermittently compressed by a flowrate control actuator in the control system assembly. An algorithm may be utilized to provide closed-loop control of a flowrate control actuator based on inputs from various sensors in the system.

Drainage flow may be maintained by employing a drain line that is substantially filled with fluid, and which has an outlet lower than its inlet, whereby a siphon effect is maintained.

Drainage flowrate measurements may be accomplished by detecting falling drops of fluid within a chamber (drip chamber, cuvette, etc.), wherein the drops are of a substantially known volume. In such an arrangement, the system may count the drops and calculate flowrate based on the number of drops over a timespan of interest (e.g., mL/hr). Drainage flowrate measurements may also be accomplished with an ultrasonic sensor, a mass flowrate sensor, or any similar sensor capable of directly or indirectly measuring flow.

Pressure measurement may be accomplished by two or more disposable pressure sensors located substantially proximate to a patient anatomical marker wherein: the pressure sensors are located within the drainage flow channel, in direct communication with patient body fluid; the pressure sensors are co-located within a housing that is affixed to the patient skin; the pressure sensors are rigidly mounted at a defined spacing, such that the difference of two sensor readings can be calculated to detect sensor faults (drift, sensor failure, occlusion, fouling, etc.); the orientation of the drainage flow channel is detected by means of an orientation sensor, whereby the expected differential pressure between two pressure sensors (based on fluid density and vertical component of sensor spacing) is calculated and used to augment pressure sensor fault detection; stable (average) pressure is derived from variable pressure readings (such as may be observed from an ICP waveform, blood pressure systolic/diastolic pressure spikes, etc.) via a proprietary algorithm.

In certain embodiments, the system may be configured to monitor and/or control pressure or flowrate of a single fluid (CSF, blood, urine, etc.). In other embodiments, the system may be configured to monitor and/or control two or more fluids or anatomical subsystems (CSF and blood; bladder pressure and intra-abdominal pressure; etc.). In certain embodiments, the system may include calculation of a derived parameter, such as perfusion pressure (CPP, APP, SCPP, etc.), and may monitor and/or control pressure or flowrate of a single fluid or body compartment based on said derived parameter. In certain embodiments, the system may include a peristaltic or similar pumping mechanism for control of fluids other than the target body fluid (saline, artificial CSF, etc.) for the purposes of periodic flushing, back-pressure (as may be the case with an arterial line), etc.

1. Control System Assemblies

Control system assemblies disclosed herein comprise, in certain embodiments, (1) a fluid flow detection and control subassembly that is in operable communication with (2) a user interface subassembly to achieve the real-time monitoring and control of body fluid pressure and drainage. In certain aspects of these control system assemblies, the fluid flow detection and control subassembly comprises, in operable communication, a primary flowrate control actuator, a secondary flow shutoff actuator, and a body fluid flow sensor.

Figure 2:
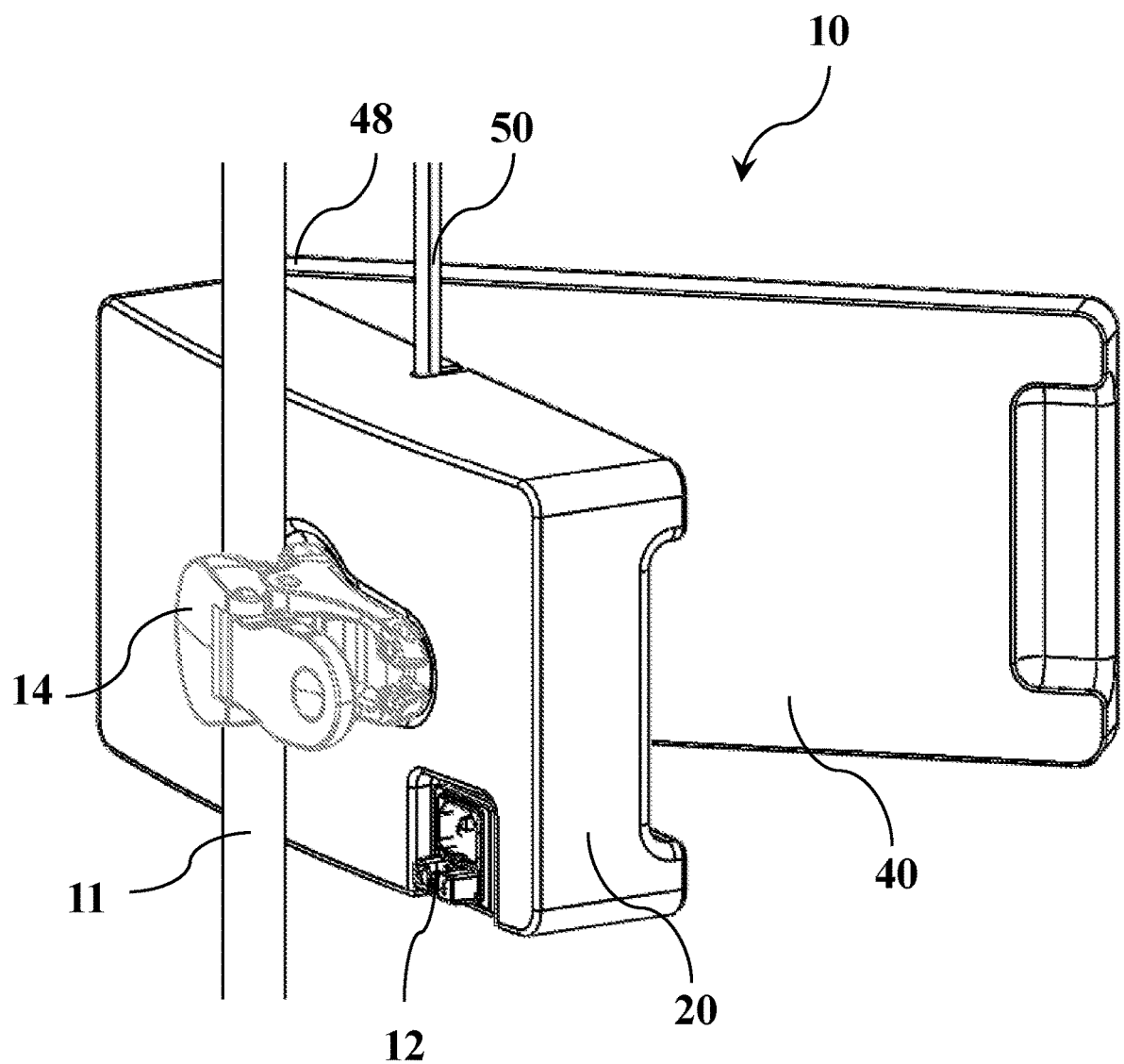
FIG. 2 is a line drawing showing a rear perspective view of a control system assembly according to certain embodiments of the presently disclosed body fluid management systems.
Figure 4:
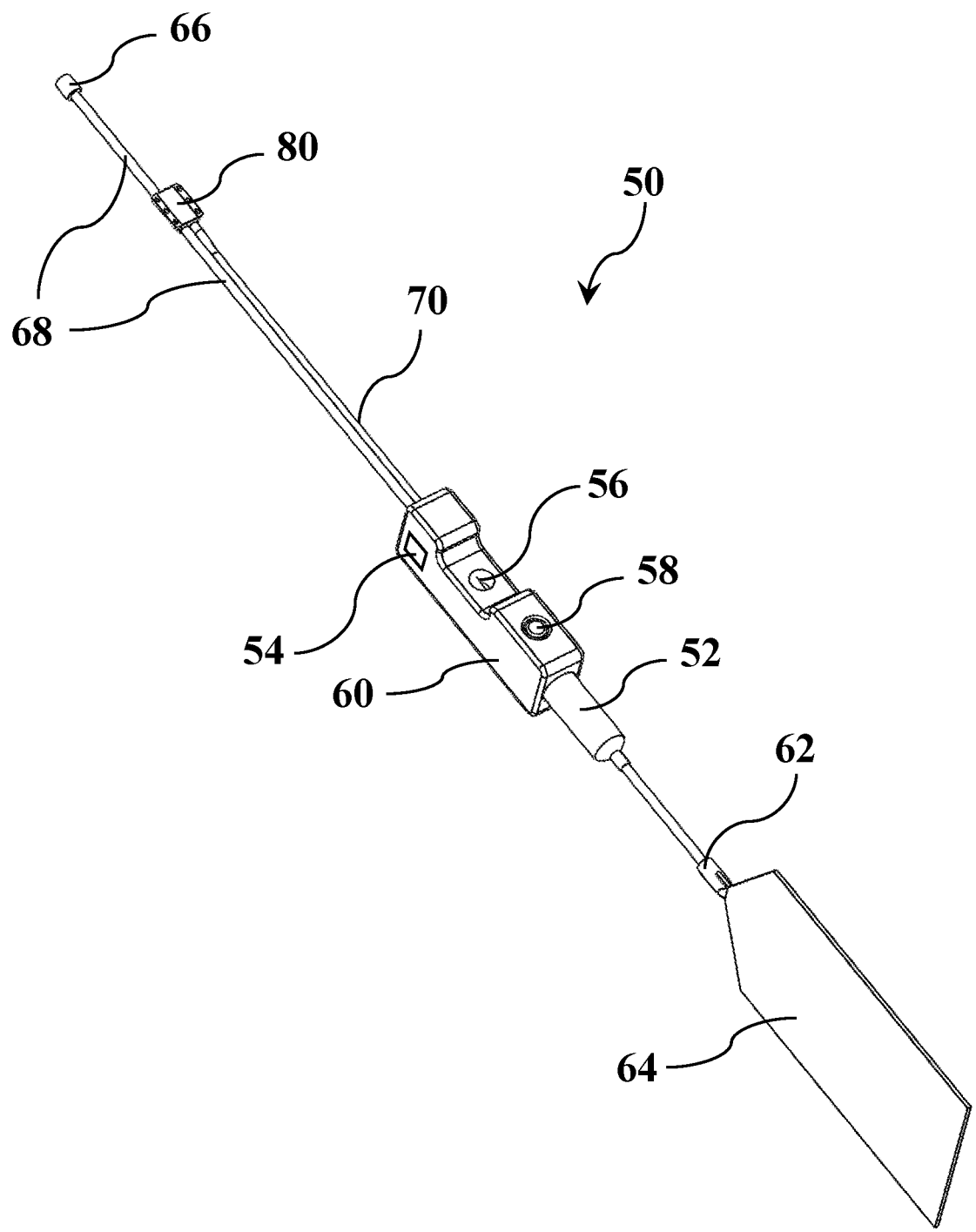
FIG. 4 is a line drawing showing a perspective view of a patient interface assembly according to one embodiment of the presently disclosed portable systems for managing body fluid pressure and drainage flowrates.

FIG. 1 and FIG. 2 are line drawings showing perspective views of an exemplary control system assembly 10 that is configured for use in operable combination with a patient interface assembly 50 (such as is depicted in FIG. 4 and described elsewhere herein) according to certain embodiments of the presently disclosed body fluid management systems.

As depicted in FIG. 1, control system assembly 10 comprises fluid flow detection and control subassembly 20 in operable combination with user interface subassembly 40, which includes user interface 42 for receiving user input (settings, patient information, etc.) and displaying system settings and outputs (set points, alarm thresholds, patient information, current or historical pressure or flowrate data, alarms, notifications, waveforms, etc.). In certain embodiments, user interface 42 may comprise a graphical display (LCD, OLED, etc.), a touchscreen (resistive, capacitive, projected capacitive, etc.), a button keypad (plastic or elastomeric buttons, membrane switch, etc.), an LED array (7-segment, individual indicators, etc.), or any similar elements suitable for entry of user inputs and display of system settings and outputs.

As depicted in FIG. 2, control system assembly 10 comprises adjustable clamping mechanism 14 for fixation to an IV pole 11, bed rail, or other similar patient room furnishing. In other embodiments, control system assembly 10 may be configured to be cart-mounted, wall-mounted, or free-standing.

In other aspects, control system assembly 10 comprises a receptacle 12 for connection to an external power source (AC mains, DC network, etc.), and may optionally include an internal power source (rechargeable battery).

In further aspects, control system assembly 10 may include an electrical interface (connector/socket, pogo-pin/spring-loaded contact array, etc.) for DC power distribution and electrical signal communication with patient interface assembly 50. In other embodiments, such communication or power distribution may be accomplished wirelessly.

In certain embodiments, fluid flow detection and control subassembly 20 and user data interface subassembly 40 may each be enclosed in a set of rigid (plastic, metal, etc.) housings and joined by pivoting mechanism 48 (hinge, 4-bar linkage, etc.) so that the subassemblies may pivot open and closed with respect to one another. In certain embodiments, pivoting mechanism 48 may include a feature (over-center, cam, etc.) that provides one or more preferred positions (closed, fully open, etc.) to assist with installing/uninstalling fluid drainage cartridge 60. As depicted in FIG. 1, hand grip 44 and hand clearance feature 24 may be included to facilitate operation of pivoting mechanism 48. In alternate embodiments, control system 10 may be comprised of a single set of rigid housings enclosing both fluid flow detection and control assembly 20 and user interface subassembly 40 such that hinge 48, hand grip 24, and other associated features, are eliminated. In such embodiments, recess 32 for receiving fluid drainage cartridge 60 of patient interface assembly 50 may be located adjacent to graphical user interface 42.

In other aspects, fluid flow detection and control subassembly 20 includes recess 32, drainage tube inlet 34, and drainage tube outlet 26 for receiving fluid drainage cartridge 60 and associated drain tube 68 of patient interface assembly 50 (depicted in FIG. 4).

In other aspects depicted in FIG. 1, fluid flow detection and control subassembly 20 includes, in operable combination, primary flowrate control actuator 22 for controlling flowrate of a body fluid, secondary flow shutoff actuator 30 for automatic shutoff of drainage flow in the case of power loss or system failure, and body fluid flow detector 28 for detecting drainage flowrate.

In certain embodiments, body fluid flow detector 28 may be an optical sensor for detecting falling fluid drops (as in drops falling through a drip chamber, cuvette, or similar enclosure), a mass flow sensor, an ultrasonic flow sensor, or any other similar sensor that is capable of detecting flow of the target body fluid with clinically-acceptable precision and accuracy.

In certain embodiments, secondary flow shutoff actuator 30 may be a DC motor with encoder and leadscrew, a stepper motor with leadscrew, a servo motor, a solenoid, a linear actuator, an electromagnetic latch, or any other similar actuator or latching mechanism that can be actuated sufficiently rapidly to shut off flow in the case of power loss or system failure.

In certain embodiments, primary flowrate control actuator 22 may be a DC motor with encoder and leadscrew, a stepper motor with leadscrew, a servo motor, a solenoid, a linear actuator, or any other similar actuator that either provides precise positioning for substantially constant flowrate (as in the case of a motor with encoder, stepper, or servo) or can be actuated rapidly between on/off states for intermittent flow (as in the case of a solenoid).

FIG. 3A and FIG. 3B depict an exemplary primary flowrate control actuator 22 that may be advantageously employed in control system assembly 10 according to certain embodiments of the presently disclosed body fluid management systems. As shown in FIG. 3A, primary flowrate control actuator 22 may be comprised of a stepper motor 92 with integrated leadscrew 96 and captive leadscrew nut 94 to translate rotary motion into linear motion. Pinch head 98 comprising pinch head tip 100 may be included to interface with drain tube 68 in patient interface assembly 50 (depicted in FIG. 4). In other embodiments, pinch head 98 may be replaced with spring-loaded pinch head 102 as shown in FIG. 3B to improve flow control precision or provide substantially constant force at the fully pinched condition regardless of any over-travel of the primary flow control actuator.

In other embodiments, flow control or shutoff may be accomplished by a rotary valve (stopcock, needle valve, etc.) in patient interface assembly 50 that is variably rotated by a rotary actuator (servo, stepper motor, rotary solenoid, etc.) in control assembly 10.

2. Patient Interface Assemblies

Patient interface assemblies for use in the body fluid management systems disclosed herein comprise, in various operable combinations: (1) a body fluid flow measurement interface, (2) a flowrate control actuator interface, (3) a flow shutoff actuator interface, (4) an electrical interface, (5) a fluid drainage cartridge, (6) a drain tube, and (7) a wearable pressure sensor subassembly. In certain aspects of these patient interface assemblies, the wearable pressure sensor subassembly comprises, in operable communication: (1) an orientation sensor, (2) a plurality of pressure sensors, (3) an integrated flow channel, and (4) a rigid or semi-rigid sensor enclosure.

FIG. 4 is a line drawing showing a perspective view of patient interface assembly 50 according to one embodiment of the presently disclosed body fluid management system, wherein patient interface assembly 50 is configured for removable insertion into, and operable combination with, control system assembly 10. In certain embodiments, fluid drainage cartridge 60 (comprised primarily of rigid plastic enclosures such as ABS, nylon, polycarbonate, etc.) of patient interface assembly 50 may be installed into a corresponding recess in control system assembly 10, such as recess 32 depicted in FIG. 1.

As depicted in FIG. 4 patient interface assembly 50 may comprise flow measurement interface 52 (drip chamber, cuvette, tube, etc.) for interfacing with flow measurement detector 28 of control assembly 10, flowrate control actuator interface 56 (soft flexible tube, such as silicone, polyurethane, polypropylene-based elastomer, etc.) for interfacing with pinch head 100 of primary flowrate control actuator 22 within control system assembly 10, and flow shutoff actuator interface 58 (spring-loaded button, stopcock, pinch valve, etc.) for interfacing with secondary flow shutoff actuator 30 of control assembly 10. Fluid drainage cartridge 60 may further comprise drain tube 68 (silicone, polyurethane, polypropylene-based elastomer, etc.), connected at its inlet end to detachable fitting 66 (luer fitting, neuro fitting, etc.) for interfacing with an implanted ventricular catheter, and connected at its outlet end to detachable drain bag 64 (polyethylene, PVC, etc.) for collecting body fluids.

Patient interface assembly 50 may also include electrical cable 70 between wearable pressure sensor subassembly 80 and fluid drainage cartridge 60, and a set of exposed conductive pads 54 (gold, copper, carbon, silver ink, etc.) on fluid drainage cartridge 60 for passing electrical signals, data, power, etc. between patient interface assembly 50 and control system assembly 10. In such embodiments, a corresponding set of spring contacts (pogo pins, battery-style contacts, etc.) in control system assembly 10 may interface with said conductive pads in the patient interface assembly. Other embodiments of fluid drainage cartridge 60 may alternatively comprise a traditional electrical connector that is manually inserted into a corresponding receptacle in the control system assembly 10 by the user. Yet other embodiments may replace the physical electrical interface altogether by implementing wireless communication (Bluetooth, Wi-Fi, etc.) between patient interface assembly 50 and control system assembly 10, or between patient interface assembly 50 and a remote control system (cloud-based system, on-site or off-site server, smartphone or tablet-based application, etc.). In such arrangements, wearable pressure sensor subassembly 80 may be powered with a battery or similar power source.

Figure 5:
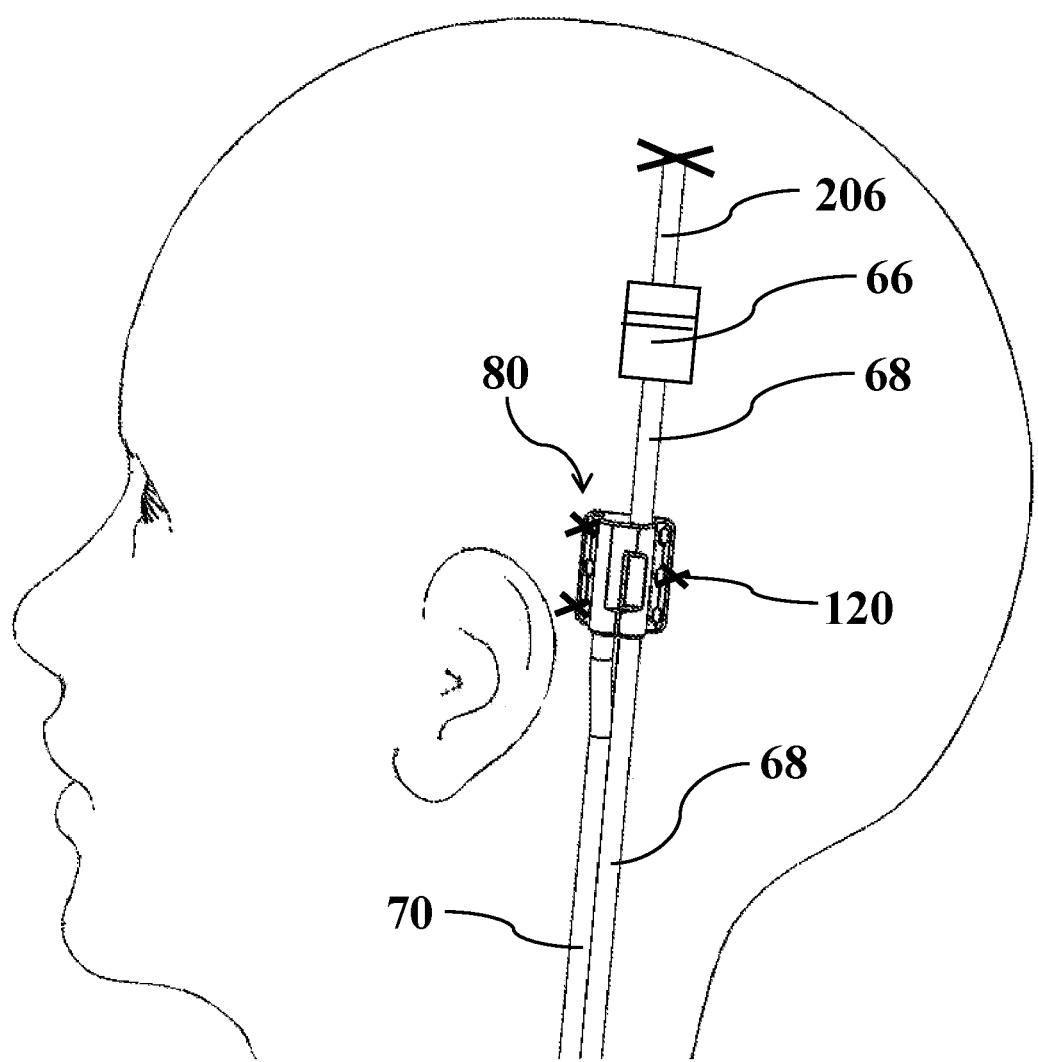
FIG. 5 is a line drawing that depicts an embodiment of the patient interface assembly as it relates to the patient anatomy, wherein the pressure sensor assembly is sutured directly to the patient's skinon the head substantially proximate to a known anatomical marker.

FIG. 5 is a line drawing that depicts an aspect of patient interface assembly 50 as it relates to the patient anatomy, wherein the proximal end of drainage tube 68 is separably connected via detachable fitting 66 to an implanted ventricular catheter 206, and wherein wearable pressure sensor subassembly 80 is affixed directly to the patient's skin substantially proximate to a known anatomical marker (EAM, etc.) by sutures 120. In other embodiments, direct fixation of the wearable pressure sensor assembly may be accomplished by an adhesive patch (acrylic, etc.) with peel-off backing, or a separate liquid adhesive (cyanoacrylate, etc.) that is applied between the patient's skin and the wearable pressure sensor assembly housing. The patient fixation feature may alternatively be on a separable component, such that the wearable pressure sensor assembly is affixed (snapped, fastened, hook-and-loop fastener, etc.)

to/into the separable fixation component after it is affixed (sutured, bonded, etc.) to the patient.

Figure 6:
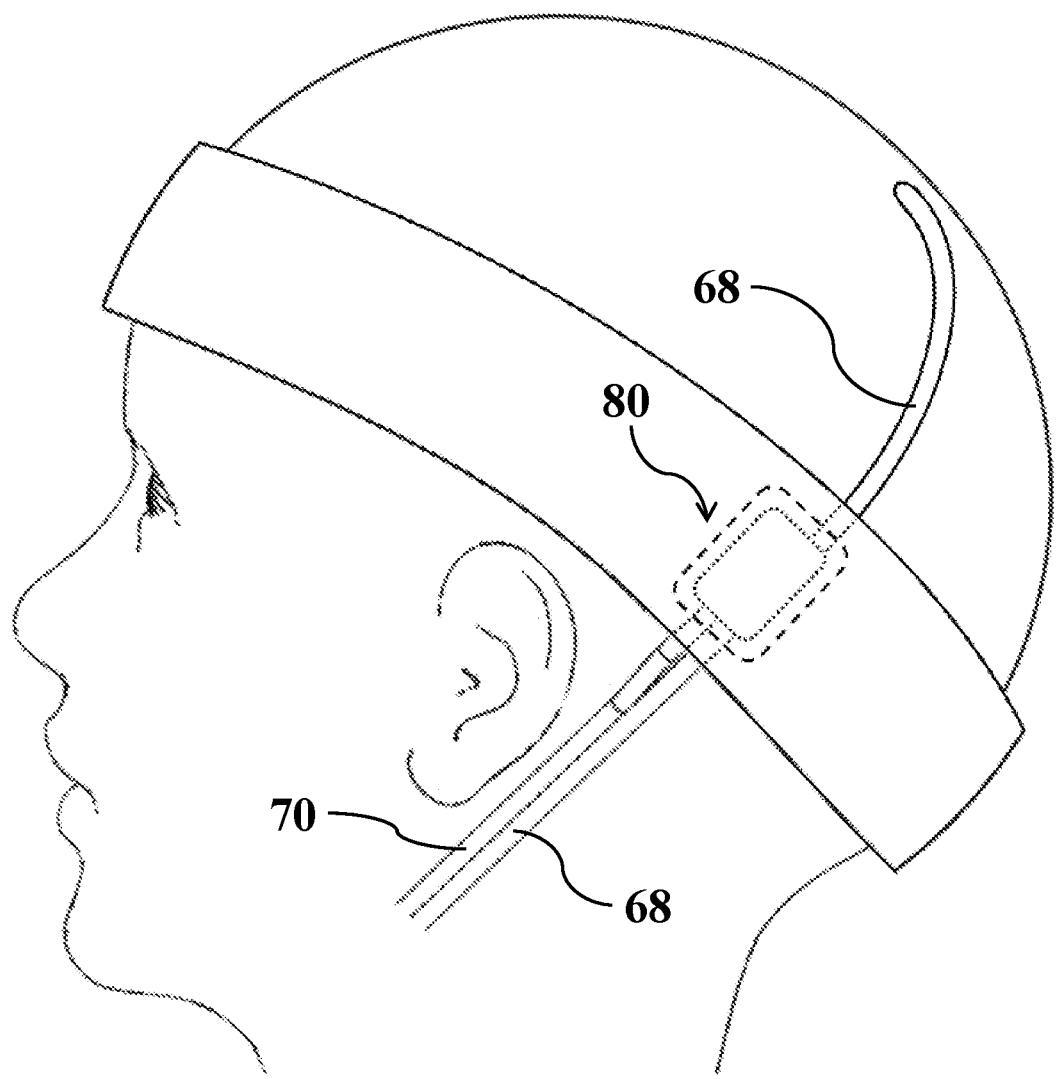
FIG. 6 depicts alternate embodiments in which the pressure sensor assembly is constrained near an anatomical marker by means of a wearable device.
Figure 7:
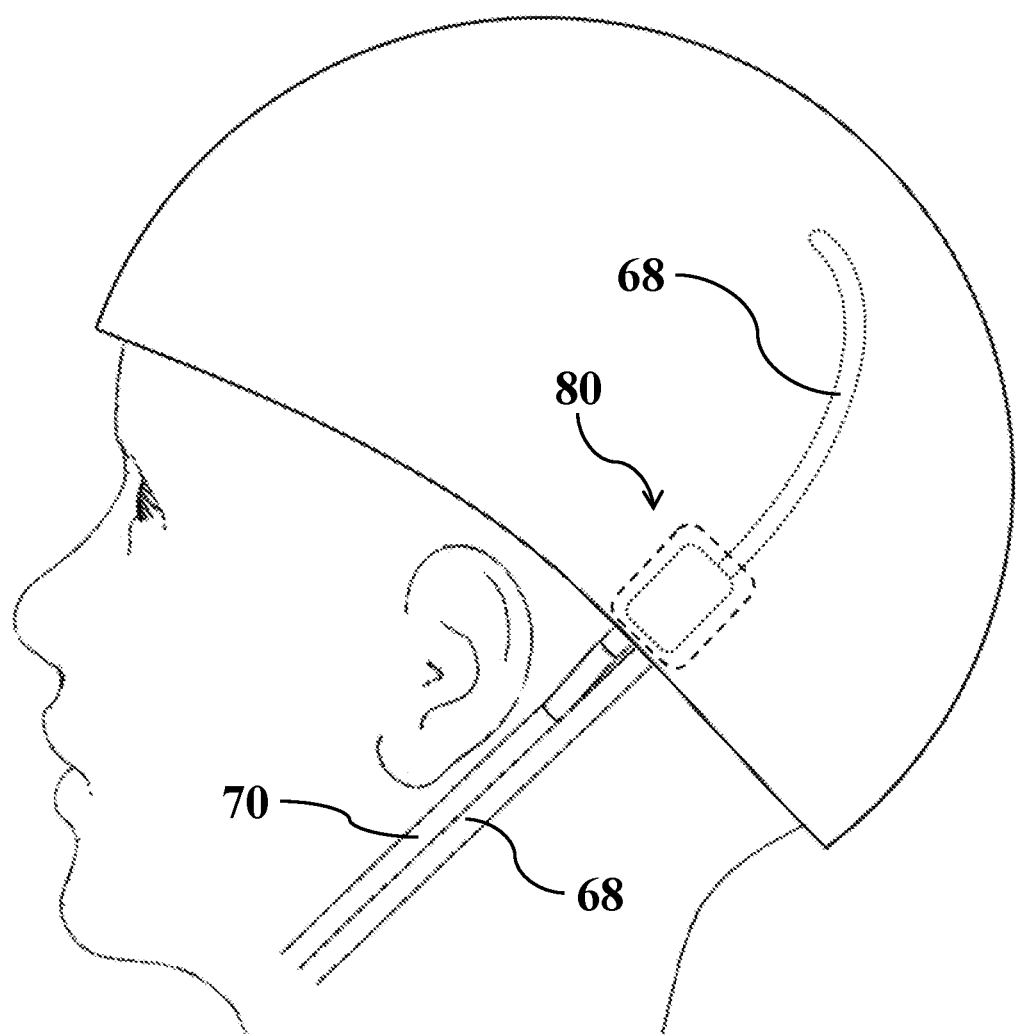
FIG. 7 depicts alternate embodiments in which the pressure sensor assembly is constrained near an anatomical marker by means of a wearable device.

FIG. 6 and FIG. 7 depict alternate embodiments in which wearable pressure sensor subassembly 80 is constrained near an anatomical marker by means of a wearable device such as a headband or a hat (beanie, skull cap, etc.). Such wearable devices may be comprised of foam, silicone, fabric, hook-and-loop, mesh, gauze, etc.

Figure 8:
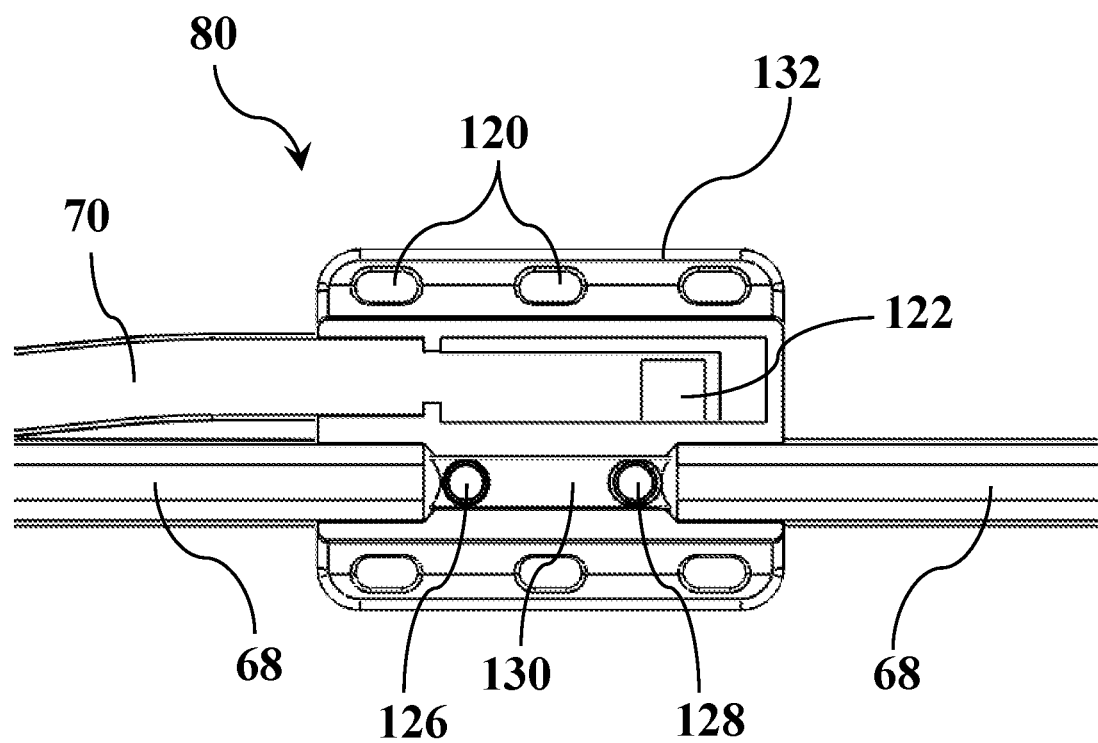
FIG. 8 is a line drawing of an exemplary wearable pressure sensor subassembly for use in certain embodiments of the patient interface assemblies disclosed herein.

FIG. 8 depicts an embodiment of wearable pressure sensor subassembly 80 of patient interface assembly 50 (as depicted in FIG. 4), wherein pressure sensor subassembly 80 comprises a sensor array of two or more pressure sensors 126 and 128 for measuring a single body fluid pressure (ICP, blood pressure, bladder pressure, etc.) and an orientation sensor 122 (accelerometer, tilt sensor, etc.) for detecting the orientation of flow channel 130. Wearable pressure sensor subassembly 80 may be contained (by bonding, mechanical fastening, over-molding, etc.) within a rigid (plastic, metal, etc.) or semi-rigid (silicone, polyurethane, etc.) enclosure 132, which includes integrated flow channel 130 with an inlet and outlet to which drain tube 68 is permanently affixed (UV bonding, solvent bonding, epoxy, etc.), and one or more suture points 120 for attaching to a patient proximate to an anatomical marker (EAM, midaxillary, etc.). In various embodiments, the sensor array of wearable pressure sensor subassembly 80 may be constructed upon a suitable substrate (polyimide, polyester, FR-4, etc.) according to traditional electronics-fabrication methods known in the art. In various other embodiments, sensors may be mounted directly onto enclosure 132 using various other methods known in the art such as in-mold printed electronics, conductive inks/epoxies, etc. In other aspects, pressure sensors 126 and 128 or orientation sensor 122 may produce digital electrical signals using a standard communications protocol known in the art (SPI, I2C, UART, etc.), or may produce an analog signal that is converted to a digital signal by an analog-to-digital converter.

In some embodiments, wearable pressure sensor subassembly 80 may additionally include contact plates, a capacitive switch, or similar sensing element to detect whether the assembly is in contact with the skin. Such a feature may be useful for detecting certain faults, such as whether the pressure sensor assembly has fallen off the patient and may not be reading the proper pressure value.

FIG. 9A and FIG. 9B are schematic representations of wearable pressure sensor subassembly 80 according to certain embodiments of the present disclosure, wherein an orientation sensor (A) and a plurality of pressure sensors (P1 and P2) are mounted at a fixed spacing distance (d) onto a rigid or semi-rigid member (B). FIG. 9A depicts wearable pressure sensor subassembly 80 in a horizontal orientation with respect to gravity vector (g). FIG. 9B depicts wearable pressure sensor subassembly 80 in a vertical orientation with respect to gravity vector (g).

Within certain aspects of this embodiment, the orientation sensor detects the orientation of wearable pressure sensor subassembly 80 thereby facilitating calculation of an anticipated pressure differential ΔP according to the formula:

$$\Delta P_{anticipated} = \rho(\Delta h)$$

wherein ρ is the fluid density (e.g., the density of CSF, saline, blood, urine, etc.) and Δh is the height differential between pressure sensors P2 and P1 with respect to the gravity vector.

As depicted in FIG. 9A, when wearable pressure sensor subassembly 80 is oriented horizontally with respect to the gravity vector (g), the pressure readings of the plurality of pressure sensors (P1 and P2) are substantially equivalent because the height differential (Δh) between the two pressure sensors (P1 and P2) is zero (i.e., Δh=0, so $\Delta P_{anticipated}=0$).

As depicted in FIG. 9B, when wearable pressure sensor subassembly 80 is oriented vertically with respect to the gravity vector (g), the pressure differential between the plurality of pressure sensors (P1 and P2) is maximized because the height differential (Δh) between the two pressure sensors is also maximized (i.e., Δh=d, so $\Delta P_{anticipated}=\rho d$).

In any pressure sensor orientation other than horizontal or vertical, the height differential between the plurality of pressure sensors (P1 and P2) will vary between 0 and d based on the vertical component of pressure sensor orientation with respect to the gravity vector (g). The corresponding anticipated pressure differential will range from $\Delta P_{anticipated}=0$ to $\Delta P_{anticipated}=\rho d$.

In certain embodiments of the control system algorithm, one or both pressure sensors may be used to determine actual measured fluid pressure, while any substantial deviation between $\Delta P_{anticipated}$ (as described above) and $\Delta P_{actual}$ (obtained directly via pressure sensor readings) may be used by the system to detect pressure sensor faults (electrical failure, drift in sensor accuracy, bio-fouling, etc.).

It will be apparent to one skilled in the art that the current disclosure is applicable to the measurement of gauge or absolute pressure, since either may be accomplished depending on the type of sensor used for P1 and P2, or the inclusion of separate atmospheric pressure sensor(s) outside the fluid path (such as in the control system assembly) for the calculation of gauge pressure.

The disclosed approach provides two layers of redundancy. Firstly, since each pressure sensor in wearable pressure sensor subassembly 80 is located proximate to an anatomical marker for the fluid of interest, a second pressure sensor provides a direct "backup" that may allow the system to continue operating in the event that either sensor is determined to no longer be functioning normally. Secondly, the system may detect very small amounts of drift in the accuracy of the wearable pressure sensor assembly and take appropriate action (such as notifying the user) before such errors become clinically relevant.

The disclosed approach differs from existing two-sensor systems, wherein one sensor measures the pressure in the target fluid line and a second sensor measures the pressure in a separate reference line, and wherein both pressure sensors are positioned at a location other than a relevant anatomical marker (e.g., in a pole-mounted console or hip-worn wearable). In such systems, the true pressure of the target fluid (e.g., true ICP) is calculated as the difference between the pressure in a drain line and the pressure in a separate reference line.

Previously described two-sensor arrangements provide no redundancy and limited opportunities for error-checking, leaving the patient vulnerable to sensor drift and similar faults. The co-location of two pressure sensors and an orientation sensor substantially proximate to a relevant anatomical marker as described in the current disclosure provides an unprecedented level of measurement accuracy and clinical safety.

It will be appreciated that wearable pressure sensor assembly 80 must be sufficiently small and lightweight to facilitate attachment to certain anatomical markers (such as the EAM, which is located on the head) in order to achieve practical use. As such, the use of sufficiently small pressure sensors, which are suitable for extended contact with body fluids, and which are also of sufficient accuracy and precision as to enable clinical utility, is critical to achieving the disclosed embodiments. Furthermore, the spacing distance between the sensors must be sufficiently small as to facilitate a suitable overall footprint for the assembly, which places further constraints on the precision of said pressure sensors to enable useful drift detection as described elsewhere herein. For example, a spacing distance on the order of a few centimeters is only useful if the pressure sensors are able to resolve pressure differences on the order of a few millimeters of water (mmH2O). Such pressure sensors were unknown to the art until recently, rendering such embodiments impractical. However, due to recent technological developments in the art, spacing distances (d) in the range of 1-2 cm are now possible, using tiny (2-3 mm wide) pressure sensors with precision on the order of ±1 mmH2O, enabling practical embodiments of wearable pressure sensor assemblies with an overall footprint in the range of 2-5 $cm^2$ that have the characteristics described herein.

3. Use and Configurations

Figure 10:
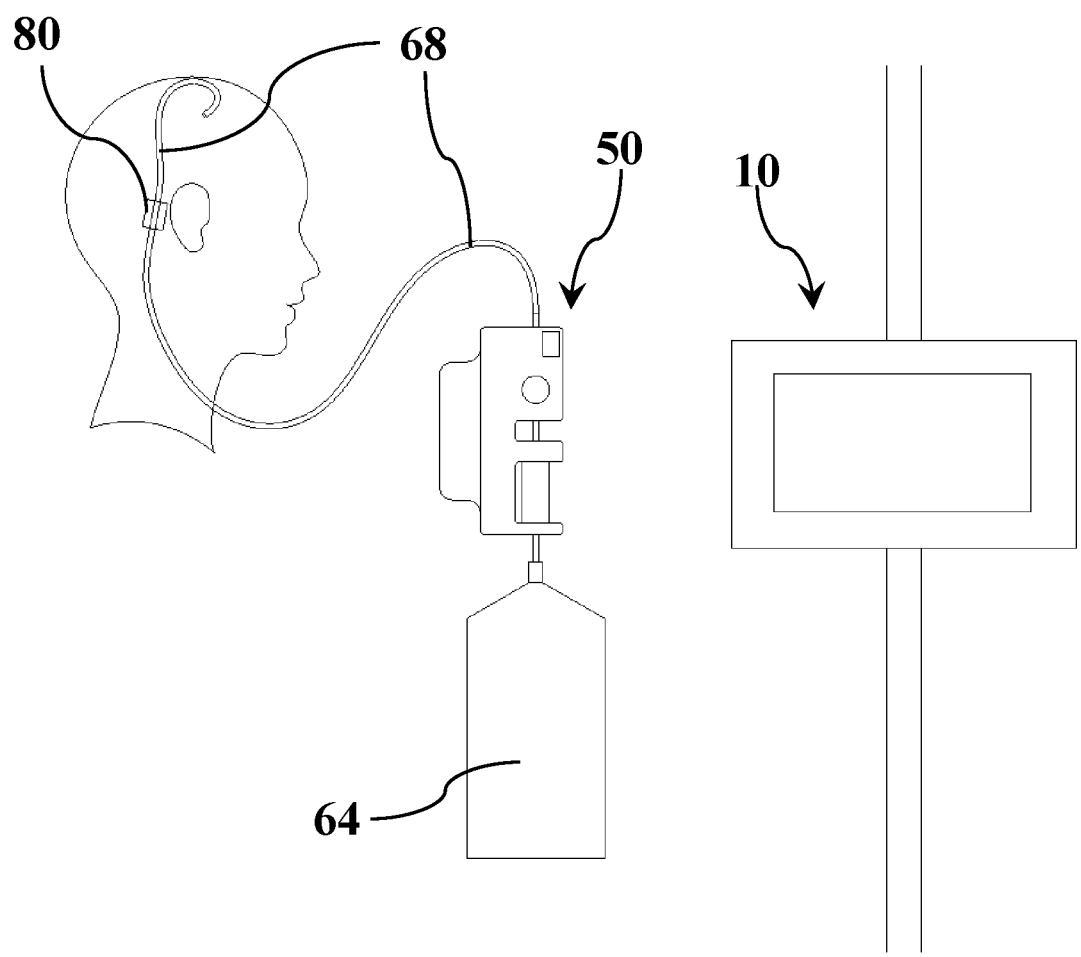
FIG. 10 depicts one embodiment of the presently disclosed body fluid management systems, which is configured for managing intracranial pressure (ICP) and cerebrospinal fluid (CSF) drainage, wherein a patient interface assembly is connected to a ventricular catheter at a proximal end of a drain tube.
Figure 11:
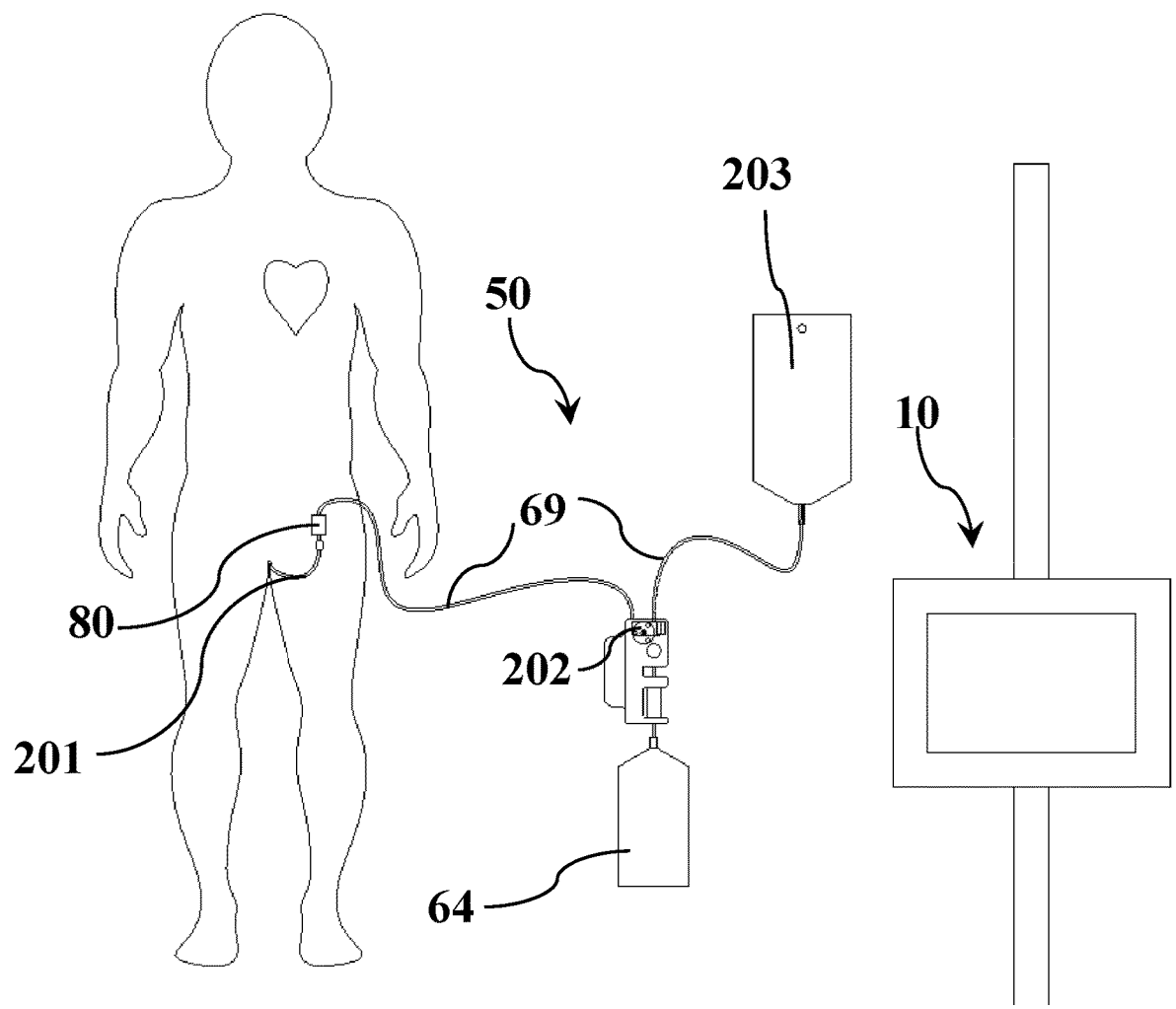
FIG. 11 depicts one embodiment of the presently disclosed body fluid management systems, in which the patient interface assembly is configured to connect to an indwelling urinary catheter, and the control system assembly is configured to activate the pumping mechanism to periodically flush the bladder and urinary catheter.
Figure 12:
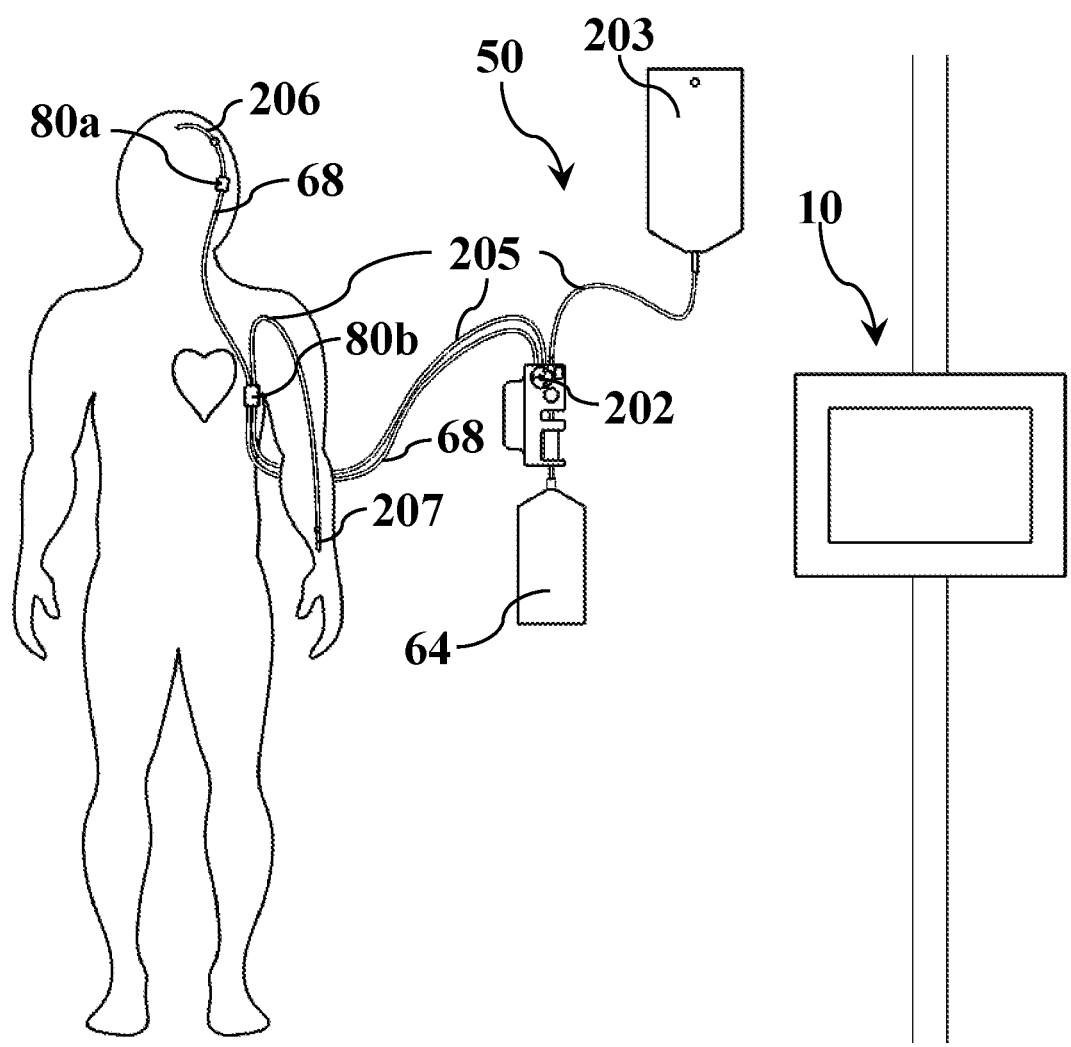
FIG. 12 depicts one embodiment of the presently disclosed body fluid management systems that is configured to obtain the necessary inputs to calculate real-time CPP wherein the systems include a plurality of wearable sensor assemblies, wherein a first wearable sensor assembly is affixed to the patient substantially proximate to an anatomical marker appropriate for monitoring ICP and a second wearable sensor assembly is affixed to the patient substantially proximate to an anatomical marker appropriate for monitoring blood pressure.

FIG. 10, FIG. 11, and FIG. 12 depict several embodiments of the disclosed body fluid management systems, which are configured for various clinical use cases.

FIG. 10 depicts one embodiment of the presently disclosed body fluid management systems, which is configured for managing intracranial pressure (ICP) and cerebrospinal fluid (CSF) drainage, wherein patient interface assembly 50 is connected to a ventricular catheter at the proximal end, and drainage collection reservoir 64 at the distal end, via drainage tube 68. The system of FIG. 10 may be configured via user-controlled set points to activate primary flowrate control actuator 22 and, thereby, allow drainage of CSF when ICP in excess of the set point is detected by wearable pressure sensor subassembly 80 attached proximate to an anatomical marker (EAM) for the Foramen of Monro. The embodiment represented by FIG. 10 may also find utility in the management of lumbar pressure (by affixing wearable pressure sensor assembly 80 near an anatomical marker appropriate for this application), and a variety of other body fluids and pressures within various body compartments.

In other embodiments, the disclosed system may additionally include a peristaltic (or similar) pumping mechanism and a connection to a detachable infusion source (infusion bag, infusion bottle, etc.). The pumping mechanism may be configured to draw on the infusion source to perform periodic infusion operations, or to provide continuous or intermittent back-pressure for certain monitoring operations. Such embodiments may find utility in a variety of clinical applications that benefit from back-pressure or periodic flushing. One example of such an arrangement is depicted in FIG. 11, wherein patient interface assembly 50 is configured to connect to an indwelling urinary catheter 201 at the proximal end, and to an infusion source 203 and drainage collection reservoir 64 at the distal end, via bidirectional infusion and drainage tube 69. The system of FIG. 11 may be configured via user-controlled set points to activate the pumping mechanism to periodically flush the bladder and urinary catheter with a certain volume of saline. Alternatively, the system may be configured such that the pumping mechanism infuses saline until a certain upper pressure threshold is detected by wearable pressure sensor assembly 80 located substantially proximate to the bladder, at which point the pumping mechanism may be deactivated to allow bladder drainage. In either case, the resultant flushing action mimics the body's natural urinary cycle by minimizing the stagnant and low-flow conditions. Furthermore, repeated cleansing of the area may substantially dilute any bacterial units that begin to colonize. Such arrangements may find utility in reducing the incidence of bladder and urinary tract infections associated with uncontrolled urinary drainage and extended urinary catheterization typical in the current clinical practice for management of patients during critical care.

The embodiment depicted in FIG. 11 may also find utility in monitoring the pressure of various body cavities for compartment syndrome in a less invasive manner than direct implantation of a pressure transducer into the cavity. For example, in the case of intra-abdominal pressure monitoring, the system controller may utilize the infusion source and pumping mechanism to slightly inflate a patient's bladder with a small quantity of saline (or similar fluid) and measure the resulting pressure response from the abdominal cavity by means of a wearable pressure sensor assembly located substantially proximate to an anatomical marker for the bladder. The bladder pressure in such an arrangement may be used as a minimally-invasive indicator of intra-abdominal pressure. The system control assembly may be further configured to periodically pause intra-abdominal pressure monitoring to allow substantially complete drainage of the bladder to ensure that appropriate urinary drainage is maintained, then re-inflate the bladder to resume intra-abdominal pressure monitoring.

In other similar embodiments, the patient interface assembly may be configured to connect to an implanted venous catheter (central line) or implanted arterial catheter (arterial line), and the control system assembly may be configured to activate the pumping mechanism to flush the blood connection line periodically or continuously with saline. Such arrangements automate and improve upon clinical practice by ensuring patency of the arterial or central line without constant clinical oversight and maintenance and ensure that pressure sensor(s) located in the line are not fouled by blood components or coagulated blood.

In certain embodiments, one or more additional pressure sensor(s) may be placed within wearable pressure sensor subassembly 80 for added redundancy, at a second anatomical marker of interest, on a separate fluid line for the measurement of multiple fluids (e.g., blood and CSF simultaneously), or at strategic locations along one or more fluid lines (such as the high point of a fluid line where air bubbles are most likely to accumulate). Such arrangements may be warranted in certain applications for enhanced patient safety, additional diagnostics or error-checking, and/or additional clinical benefit or insight.

FIG. 12 depicts yet another embodiment of the presently disclosed fluid management systems in which patient interface assembly 50 comprises primary fluid line 68 for connection to an implanted ventricular catheter 206 at its proximal end and a detachable fluid drainage reservoir 64 at its distal end. In other aspects, patient interface assembly 50 further comprises secondary fluid line 205 for connection to an implanted arterial catheter 207 at its proximal end and an infusion source 203 at its distal end. In other aspects, the patient interface assembly further comprises first wearable pressure sensor assembly 80*a*, which is affixed to the patient substantially proximate to an anatomical marker appropriate for monitoring ICP (EAM), and second wearable pressure sensor assembly 80*b*, which is affixed to the patient substantially proximate to an anatomical marker appropriate for monitoring blood pressure (fourth left intercostal space, etc.).

Each of the first and second wearable pressure sensor assemblies may include an orientation sensor for monitoring patient movement/posture and error-checking pressure sensor readings as described elsewhere herein. The inclusion of multiple orientation sensors facilitates more detailed tracking of patient posture (e.g., tracking patient trunk orientation independent of head orientation for more accurate real-time modeling of the spinal column and associated CSF pressures in 3D space). Such information may be utilized by the system control assembly to automatically adjust displayed values to reflect the true value of a particular parameter more accurately at the anatomical point of interest, or for tracking of patient movement over time (e.g., for ensuring a patient is moved with sufficient frequency to prevent pressure injuries or for monitoring a patient that may be waking from a comatose or sedated condition).

In some embodiments, the first wearable pressure sensor assembly may monitor only ICP, whereas the second wearable pressure sensor assembly may monitor both ICP and blood pressure. Such an arrangement provides a pressure reference for ICP that is normalized at the same elevation as the blood pressure reference for accurate calculation of CPP. In alternate embodiments, the second wearable pressure sensor assembly may monitor blood pressure only.

In some embodiments, the patient interface assembly may be comprised of a single integrated assembly, whereas in other embodiments the primary, secondary, and tertiary lines and their associated components may be separate patient interface assemblies. In some embodiments, various aspects of pumping mechanism 202 depicted in FIG. 11 and FIG. 12 may be divided between patient interface assembly 50 and control system assembly 10. In other embodiments, the system may be configured to monitor or control two body fluids independently (for example, to monitor intra-abdominal pressure via connection to an indwelling urinary catheter on a first fluid line as described in FIG. 11, and to independently monitor ICP and provide controlled drainage of CSF on a second fluid line as described in FIG. 10).

Embodiments of the disclosed fluid management systems such as those depicted in FIG. 12 may be further configured to use the data from the two wearable pressure sensor assemblies in combination to manage fluid pressure or drainage flowrate based on a derived parameter. For example, the system may be configured to manage CSF drainage according to CPP target setpoints and alarm thresholds, wherein instantaneous CPP is calculated in real-time using the ICP and MAP values provided by the first and second wearable pressure sensor assemblies, respectively. In other embodiments, the disclosed system may similarly be configured to manage pressure or drainage flowrate of other body fluids based on other derived parameters (spinal perfusion pressure, abdominal perfusion pressure, etc.). Systems that automatically manage fluid pressure and drainage flowrate based derived parameters (such as CPP) represent a significant advancement over the prior art, and enable exciting and useful clinical applications that are not possible or practical with existing technologies.

It will be understood that the disclosed body fluid management systems may thus be configured in a variety of ways for monitoring or managing a variety of fluids or anatomical subsystems, as may be deemed useful in clinical practice, without departing from the spirit of the disclosure.

The scope of the disclosure is thus indicated by the appended claims rather than by the foregoing description, and all changes that come within meaning and range of equivalency of the claims are intended to be embraced herein.

What is claimed is:

1. A body fluid management system, comprising:
  a. a control system assembly for real-time monitoring of a pressure of a body fluid and integrated control of drainage of said body fluid, and
  b. a patient interface assembly comprising a wearable pressure sensor subassembly configured for attaching proximate to a patient anatomical marker, said wearable pressure sensor subassembly comprising at least one pressure sensor in a body fluid path, and an orientation sensor,
  wherein said at least one pressure sensor is in direct fluid communication with said body fluid,
  wherein said orientation sensor is configured to detect an orientation of a body cavity containing said body fluid and a movement of said body cavity,
  wherein said control system assembly is configured for monitoring patient movement, patient orientation, or changes in the pressure of said body fluid based on inputs from the patient interface assembly,
  wherein said control system assembly is configured for measuring and recording a flowrate of the drainage of said body fluid,
  wherein said control system assembly is configured with an algorithm to display data, to make corrective adjustments to the flowrate of the drainage of said body fluid, or to assert an alarm based on user selected operating modes and user-defined settings,
  wherein said at least one pressure sensor comprises a first pressure sensor and a second pressure sensor in said body fluid path at a fixed spacing distance between said first pressure sensor and said second pressure sensor, and wherein said first pressure sensor, said second pressure sensor, and said orientation sensor are configured on a rigid member,
  wherein said control system assembly is configured to calculate an anticipated differential pressure between said first pressure sensor and said second pressure sensor based on said fixed spacing distance and a flow channel orientation detected by said orientation sensor,
  wherein said control system assembly is configured to calculate an actual differential pressure between said first pressure sensor and said second pressure sensor based on direct measured pressure of said body fluid, and
  wherein said control system assembly is configured for detecting drift in the first pressure sensor or the second pressure sensor based on a disparity between the anticipated differential pressure between the first pressure sensor and the second pressure sensor and the actual differential pressure between the first pressure sensor and the second pressure sensor.

2. The body fluid management system of claim 1 wherein said control system assembly comprises a fluid flow detection and control subassembly in operable communication with a user interface subassembly including graphical user interface.

3. The body fluid management system of claim 2 wherein said graphical user interface is configured to display a pressure waveform.

4. The body fluid management system of claim 2 wherein said fluid flow detection and control subassembly comprises, in operable communication, a flowrate control actuator, a flow shutoff actuator, and a body fluid flow detector.

5. The body fluid management system of claim 1 wherein said patient interface assembly further comprises a body fluid drip chamber, a fluid drainage cartridge for connecting to said control system assembly, a drain tube for the drainage of said body fluid, and an electrical cable for passing signals from said wearable pressure sensor subassembly to said fluid drainage cartridge.

6. The body fluid management system of claim 1 wherein said body fluid is cerebrospinal fluid (CSF) and wherein said control system assembly is configured for real-time monitoring of intracranial pressure (ICP) and integrated control of CSF drainage.

7. The body fluid management system of claim 6 wherein said patient anatomical marker is a patient external auditory meatus (EAM).

8. The body fluid management system of claim 1 wherein said body fluid is cerebrospinal fluid (CSF) and wherein said control system assembly is configured for real-time monitoring of spinal pressure and integrated control of CSF drainage.

9. The body fluid management system of claim 1, wherein said patient interface assembly further comprises an infusion source interface for connection to an infusion source and a bidirectional infusion and drainage tube, and wherein said control system assembly further comprises a pump for pumping liquid from said infusion source to said body cavity.

10. The body fluid management system of claim 9 wherein said control system assembly is configured for real-time monitoring of intra-abdominal pressure and wherein said patient interface assembly comprises a drain tube that is configured at its proximal end for connecting to a urinary catheter.

11. The body fluid management system of claim 10 wherein said body cavity is an abdomen.

12. A system for managing a body fluid according to perfusion pressure, said system comprising:
 a control system assembly; and
 a patient interface assembly,
 wherein said control system assembly displays real-time arterial blood pressure, real-time pressure of said body fluid, and real-time perfusion pressure of a body compartment containing said body fluid, and controls drainage of said body fluid,
 wherein said patient interface assembly comprises a first fluid line and a second fluid line,
 wherein said first fluid line is configured for connecting at its proximal end to a catheter inserted into said body compartment and for connecting at its distal end to a body fluid drainage reservoir,
 wherein said second fluid line is configured for connecting at its proximal end to a catheter fluidly connected to arterial blood and for connecting at its distal end to an infusion source,
 wherein a first flow channel and a second flow channel are disposed in said first fluid line,
 wherein a third flow channel is disposed in said second fluid line,
 wherein at least one first pressure sensor is disposed in said first flow channel and configured to be in fluid communication with said body fluid,
 wherein at least one second pressure sensor is disposed in said second flow channel and configured to be in fluid communication with said body fluid,
 wherein at least one third pressure sensor is disposed in said third flow channel and configured to be in fluid communication with said arterial blood,
 wherein said first flow channel is configured to be located proximate to a first anatomical marker suitable as an anatomical reference for monitoring a first pressure of said body fluid,
 wherein said second flow channel and said third flow channel are configured to be co-located proximate to a second anatomical marker suitable as an anatomical reference for monitoring arterial blood pressure,
 wherein said control system assembly is configured to display pressure values from the at least one first pressure sensor disposed in said first flow channel as a true pressure of body fluid in said body compartment,
 wherein said control system assembly is configured to display pressure values from the at least one third pressure sensor disposed in said third flow channel as the true pressure of said arterial blood,
 wherein said control system assembly is configured to calculate and display perfusion pressure as a difference between pressure readings from the at least one third pressure sensor disposed in said third flow channel and pressure readings from the at least one second pressure sensor disposed in said second flow channel,
 wherein said first flow channel is disposed in a first wearable pressure sensor subassembly further comprising a first orientation sensor and a first enclosure configured for attaching proximate to the first anatomical marker,
 wherein said second and third flow channels are disposed in a second wearable pressure sensor subassembly further comprising a second orientation sensor and a second enclosure configured for attaching proximate to the second anatomical marker,
 wherein the at least one first pressure sensor includes a plurality of first pressure sensors comprising a first one of said first pressure sensors and a second one of said first pressure sensors,
 wherein said first one of said first pressure sensors and said second one of said first pressure sensors are mounted in said first enclosure with a fixed spacing distance between said first one of said first pressure sensors and said second one of said first pressure sensors, and
 wherein said first one of said first pressure sensor and said second one of said first pressure sensors and said first orientation sensor are configured on a rigid member for detecting drift in said first one of said first pressure sensors or said second one of said first pressure sensors based on a disparity between an anticipated differential pressure between said first one of said first pressure sensors and said second one of said first pressure sensors and an actual differential pressure between said first one of said first pressure sensors and said second one of said first pressure sensors.

13. The system of claim 12 wherein said patient interface assembly further comprises a body fluid drip chamber, a fluid drainage cartridge for connecting to said control system assembly, a drain tube for the drainage of said body fluid, and an electrical cable for passing signals from at least one of said first and second wearable pressure sensor subassemblies to said fluid drainage cartridge.

14. The system of claim 13 wherein said control system assembly comprises a fluid flow detection and control subassembly in operable communication with a user interface subassembly including graphical user interface wherein said graphical user interface is configured to display a pressure waveform, and wherein said fluid flow detection and control subassembly comprises, in operable communication, a flowrate control actuator, a flow shutoff actuator, and a body fluid flow detector.

15. The system of claim 12 wherein said body fluid is cerebrospinal fluid (CSF) and wherein said control system assembly is configured for real-time monitoring of intracranial pressure (ICP) and mean arterial blood pressure (MAP) to derive cerebral perfusion pressure (CPP) and integrated control of CSF drainage.

16. The system of claim 12 wherein said control system assembly is configured with a pump for pumping liquid from the infusion source and an algorithm to respond to signals from the first wearable pressure sensor subassembly and the second wearable pressure sensor subassembly to make corrective adjustments to flowrate of the drainage of said body fluid or to assert an alarm based on user-defined settings.

17. A wearable pressure sensor subassembly comprising:
a flow channel in a path of a body fluid, wherein a plurality of pressure sensors are disposed in the flow channel in direct fluid communication with said body fluid; and
an orientation sensor configured to detect flow channel orientation,
wherein said plurality of pressure sensors and said orientation sensor are configured for detecting changes in pressure of said body fluid, patient movement, or patient orientation,
wherein said wearable pressure sensor subassembly is configured for attaching proximate to a patient anatomical marker,
wherein said plurality of pressure sensors comprises a first pressure sensor and a second pressure sensor,
wherein said first pressure sensor is configured to measure a first pressure of said body fluid,
wherein said second pressure sensor is configured to measure a second pressure of said body fluid,
wherein an anticipated differential pressure between said first pressure sensor and said second pressure sensor is detectable based on the flow channel orientation detected by said orientation sensor,
wherein said first pressure sensor and said second pressure sensor are mounted at a fixed spacing distance between the first pressure sensor and the second pressure sensor, and
wherein said plurality of pressure sensors and said orientation sensor are configured on a rigid member for detecting drift in said first pressure sensor and said second pressure sensor based on a disparity between the anticipated differential pressure between the first pressure sensor and the second pressure sensor and an actual differential pressure between the first pressure sensor and the second pressure sensor based on the first pressure of said body fluid measured by said first pressure sensor and the second pressure of said body fluid measured by said second pressure sensor.

18. The wearable pressure sensor subassembly of claim 17 wherein said patient anatomical marker is an external auditory meatus (EAM) and wherein said plurality of pressure sensors and said orientation sensor are configured for detecting changes in intracranial pressure (ICP).

* * * * *